United States Patent
Rose et al.

(10) Patent No.: US 9,974,743 B2
(45) Date of Patent: May 22, 2018

(54) DEVICE AND METHOD FOR DELIVERY OF A MEDICAMENT

(75) Inventors: Jed E. Rose, Durham, NC (US); Seth D. Rose, Tempe, AZ (US); James Edward Turner, San Antonio, TX (US); Thangaraju Murugesan, Cary, NC (US)

(73) Assignee: Philip Morris Products S.A., Neuchatel (CH)

( * ) Notice: Subject to any disclaimer, the term of this patent is extended or adjusted under 35 U.S.C. 154(b) by 1275 days.

(21) Appl. No.: 13/497,440

(22) PCT Filed: Aug. 31, 2010

(86) PCT No.: PCT/US2010/047271
§ 371 (c)(1),
(2), (4) Date: Jun. 26, 2012

(87) PCT Pub. No.: WO2011/034723
PCT Pub. Date: Mar. 24, 2011

(65) Prior Publication Data
US 2012/0255567 A1    Oct. 11, 2012

Related U.S. Application Data

(60) Provisional application No. 61/243,087, filed on Sep. 16, 2009, provisional application No. 61/242,863, filed on Sep. 16, 2009.

(51) Int. Cl.
*A24F 47/00* (2006.01)
*A61K 9/12* (2006.01)
(Continued)

(52) U.S. Cl.
CPC ............... *A61K 9/12* (2013.01); *A24F 47/00* (2013.01); *A61K 9/0073* (2013.01);
(Continued)

(58) Field of Classification Search
None
See application file for complete search history.

(56) References Cited

U.S. PATENT DOCUMENTS

| 830,626 A | 9/1906 | Van Nes |
| 3,258,015 A * | 6/1966 | Drummond ........... A24F 47/004 |
| | | 131/273 |

(Continued)

FOREIGN PATENT DOCUMENTS

| EP | 0148749 A2 | 7/1985 |
| EP | 0354661 A2 | 2/1990 |

(Continued)

OTHER PUBLICATIONS

Hellani, et al., "Free-Base and Protonated Nicotine in Electronic Cigarette Liquids and Aerosols", Chem. Res. Toxicol., 2015, American Chemical Society, 28 (8) pp. 1532-1537.*

(Continued)

*Primary Examiner* — Michael J Felton
(74) *Attorney, Agent, or Firm* — Mueting, Raasch & Gebhardt, P.A.

(57) ABSTRACT

The disclosure relates to an improved method of enhancing nicotine concentrations in a gaseous carrier. The methods are adaptable to the delivery of nicotine for therapeutic effect in various diseases, in particular nicotine for tobacco product use cessation, substitution and/or harm reduction. The disclosure further relates various devices and device design principles for practicing these methods.

22 Claims, 14 Drawing Sheets

(51) Int. Cl.

| | | |
|---|---|---|
| *A61K 31/465* | (2006.01) | |
| *A61K 47/12* | (2006.01) | |
| *A61K 9/00* | (2006.01) | |
| *A61M 15/06* | (2006.01) | |
| *A61M 11/04* | (2006.01) | |
| *A61M 15/00* | (2006.01) | |
| *A61M 11/00* | (2006.01) | |

(52) U.S. Cl.
CPC ............ *A61K 31/465* (2013.01); *A61K 47/12* (2013.01); *A61M 11/041* (2013.01); *A61M 15/00* (2013.01); *A61M 15/06* (2013.01); *A61M 11/007* (2014.02); *A61M 11/042* (2014.02); *A61M 11/047* (2014.02); *A61M 15/002* (2014.02); *A61M 2205/3368* (2013.01); *A61M 2205/8206* (2013.01); *A61M 2209/045* (2013.01)

(56) References Cited

U.S. PATENT DOCUMENTS

| | | | |
|---|---|---|---|
| 3,356,094 A | 12/1967 | Ellis et al. | |
| 4,715,387 A | 12/1987 | Rose | |
| 4,765,348 A | 8/1988 | Honeycutt | |
| 4,830,028 A | 5/1989 | Lawson et al. | |
| 4,836,224 A | 6/1989 | Lawson et al. | |
| 4,924,886 A | 5/1990 | Litzinger | |
| 4,955,397 A | 9/1990 | Johnson et al. | |
| 5,033,483 A | 7/1991 | Clearman et al. | |
| 5,101,838 A | 4/1992 | Schwartz et al. | |
| 5,105,834 A | 4/1992 | Saintsing et al. | |
| 5,133,368 A | 7/1992 | Neumann et al. | |
| 5,327,915 A | 7/1994 | Porenski et al. | |
| 5,538,020 A | 7/1996 | Farrier et al. | |
| 6,102,036 A | 8/2000 | Slutsky et al. | |
| 6,284,262 B1 * | 9/2001 | Place | A61K 9/0056 424/435 |
| 6,772,756 B2 | 8/2004 | Shayan | |
| 6,929,004 B1 | 8/2005 | Bonney et al. | |
| 6,990,978 B2 | 1/2006 | Shayan | |
| 7,168,431 B2 | 1/2007 | Li et al. | |
| 2002/0017295 A1 | 2/2002 | Weers et al. | |
| 2004/0009128 A1 | 1/2004 | Rabinowitz et al. | |
| 2004/0034068 A1 | 2/2004 | Warchol et al. | |
| 2005/0053665 A1 | 3/2005 | Ek et al. | |
| 2005/0267120 A1 | 12/2005 | Stenkamp et al. | |
| 2006/0018840 A1 | 1/2006 | Lechuga-Ballesteros et al. | |
| 2006/0027243 A1 | 2/2006 | Matsufuji et al. | |
| 2006/0032501 A1 | 2/2006 | Hale et al. | |
| 2007/0062548 A1 | 3/2007 | Horstmann et al. | |
| 2008/0241255 A1 * | 10/2008 | Rose | A61K 31/4439 424/489 |
| 2013/0276804 A1 | 10/2013 | Hon | |

FOREIGN PATENT DOCUMENTS

| | | |
|---|---|---|
| EP | 0712584 A2 | 5/1996 |
| GB | 248751 A | 8/1926 |
| GB | 2199229 A | 7/1988 |
| JP | H01104153 A | 4/1989 |
| JP | H02190178 A | 7/1990 |
| JP | 2005522206 A | 7/2005 |
| JP | 2007512880 A | 5/2007 |
| KR | 19980008081 | 4/1998 |
| RU | 2336001 C2 | 10/2008 |
| WO | WO 03/055486 | 7/2003 |
| WO | 2004091325 A1 | 10/2004 |
| WO | 2006070288 A2 | 7/2006 |
| WO | 2007042941 A2 | 4/2007 |
| WO | 2008121610 A1 | 10/2008 |
| WO | 2010107613 A1 | 9/2010 |

OTHER PUBLICATIONS

Stevenson, Terrell; Proctor, Robert, "The Secret and soul of Marlboro", Am J Public Health, Jul. 2008, 98(7): 1184-1194, accessed on Apr. 11, 2017 via: https://www.ncbi.nlm.nih.gov/pmc/articles/PMC2424107/.*

Japanese Examination Report dated Sep. 5, 2014 issued in related JP Application No. 2012-500827, with English translation.

Battelle Memorial Institute, Research Proposal regarding Project Ariel, Produced during Minnesota Tobacco Litigation Case No. C1-04-8565, document dated Jan. 3, 1962.

Glantz, Stanton A., et al., Chapter 3 Addiction and Cigarettes as Nicotine Delivery Devices, The Cigarette Papers, 1996, 74-77, University of California Press, Berkeley, USA, available in full at: http://publishing.cdlib.org/ucpressedbooks/view?docId=ft8489p25j;brand=eschol.

Hughes, T.W., et al., Nicotine Administration Ariel Smoking Devices, Produced during Minnesota Tobacco Litigation Case No. C1-04-8565, document dated Jul. 28, 1966.

Reuter, B. [Title Unknown], The Legcy Tobacco Documents Library, May 24, 1999, pp. 1-12, Univeristy of California, San Francisco, available at http://legacy.library.uscf.edu/tid/mzf12a00.

Crouse et al., "Nicotine Extraction Preliminary Study of Methods for High Nicotine Leaf Extraction", Lorillard Research Center Greensboro, Jun. 29, 1976.

Office Action issued in Israeli for Application No. 218661 dated Apr. 18, 2016 (5 pages). English translation included.

* cited by examiner

DEVICE AND METHOD FOR DELIVERY OF A MEDICAMENT

This Application is a National Phase Application of International Application No. PCT/US2010/047271 filed Aug. 31, 2010 which claims benefit of priority to U.S. Provisional Patent Application Ser. No. 61/243,087, filed Sep. 16, 2009, and also to U.S. Provisional Patent Application Ser. No. 61/242,863, filed Sep. 16, 2009, both of which applications are incorporated by reference herein in their entirety.

TECHNICAL FIELD

The invention relates to devices and methods for delivering a medicament to a user. More particularly, the invention relates to devices and methods for delivering an aerosol of a medicament to a user's lungs.

BACKGROUND ART

Pulmonary drug delivery systems have been used for decades to deliver medicaments for the treatment of respiratory disorders. The principle behind pulmonary drug delivery is aerosolization of drug compounds to be delivered to bronchioles and alveoli. Despite facing challenges like particle size optimization and degradation, a number of companies have developed technologies to deliver treatments for diabetes, migraine, osteoporosis and cancer.

The available delivery systems include metered dose inhalers (MDIs), dry powder inhalers (DPIs), and nebulizers. MDIs were among the first to be introduced in the United States in the mid 1950s. The HFA-based (pressurized) MDI was introduced in the United States in 1995. Although DPIs were introduced in the 1970s, their use has been limited due to the overwhelming dominance of MDIs. Nebulizers are generally used within hospital settings. Technological advances within the pulmonary drug delivery technologies markets are taking place in non-CFC-based MDIs, DPIs, and liquid-based inhalers (LBIs).

Many preclinical and clinical studies have demonstrated that pulmonary delivery of medicaments is an efficient method for the treatment of both respiratory and systemic diseases. The many advantages of pulmonary delivery are well recognized and include rapid onset, patient self-administration, reduced side-effects, ease of delivery by inhalation, and the elimination of needles.

Nevertheless, methods for the administration of most medicaments have not significantly deviated from delivery via the traditional intravenous/intramuscular and oral routes to include pulmonary delivery via inhalation. The use of pulmonary delivery has been limited mainly to the administration of medicaments for the treatment of asthma.

It has been reported that in order to deliver a powder directly into the lower respiratory regions the powder should generally have a particle size of less than 5 µm. Further, powders in the 5-10 µm range have been found not to penetrate as deeply and instead tend to stimulate the upper respiratory tract regions.

When manufacturing drug formulations for dry powder inhalers (DPIs), the medicament must first be milled to obtain an acceptable particle size for pulmonary delivery. This micronization step can cause problems during manufacture. For example, the heat produced during milling can cause degradation of the medicament. Additionally, metal can rub off some mills and contaminate the medicament. Furthermore, due to the small size of the particles, dry powder formulations tend to agglomerate, especially in the presence of moisture.

Agglomeration results in low flowability of the particles which diminishes the efficacy of the dry powder formulation. As a result, careful supervision is required during milling, blending, powder flow, filling and even administration to ensure that the dry powder aerosols are properly delivered.

Thus, there is a need for new methods to prepare aerosols for medicament delivery. The present disclosure describes in part a method for combining nicotine or other medicaments with a delivery enhancing compound in a gaseous stream to generate an aerosol for pulmonary delivery, without the need for excipients or other additives including solvents.

DISCLOSURE OF INVENTION

Brief Summary of the Invention

In some embodiments, the disclosure relates to a method of delivering nicotine to a subject by inhalation, the method comprising the steps of:

a) first placing a gaseous carrier comprising a delivery enhancing compound in communication with a nicotine source comprising the nicotine, and
b) second providing the gaseous carrier comprising the nicotine to a subject.

In some embodiments, the disclosure relates to the method of paragraph [0010], further comprising the step of placing the gaseous carrier in communication with a delivery enhancing compound source comprising the delivery enhancing compound.

In some embodiments, the disclosure relates to the method of [0011], wherein the step of placing the gaseous carrier in communication with the delivery enhancing compound source precedes the step of placing the gaseous carrier comprising the delivery enhancing compound in communication with the nicotine source.

In some embodiments, the disclosure relates to the method of [0010], [0011], or [0012], wherein the delivery enhancing compound source comprises a plurality of compartments comprising two or more precursor compounds.

In some embodiments, the disclosure relates to the method of [0013], wherein the delivery enhancing compound comprises ammonium chloride and the two or more precursor compounds include ammonia and hydrogen chloride.

In some embodiments, the disclosure relates to the methods of [0010]-[0013], or [0014], wherein the nicotine concentration in the gaseous carrier is increased relative to the nicotine concentration that would be contained in the gaseous carrier without the delivery enhancing compound.

In some embodiments, the disclosure relates to the methods of [0010]-[0014], or [0015], wherein the delivery enhancing compound comprises an acid.

In some embodiments, the disclosure relates to the method of [0016], wherein the acid is an organic acid.

In some embodiments, the disclosure relates to the method of [0017], wherein the organic acid has a greater vapor pressure than nicotine base at a given temperature.

In some embodiments, the disclosure relates to the method of [0018], wherein the given temperature is 25, 30, 40, 45, 70 or 100 degrees C.

In some embodiments, the disclosure relates to the methods of [0016]-[0018], or [0019] wherein the acid is selected from the group consisting of 3-Methyl-2-oxovaleric acid, Pyruvic acid, 2-Oxovaleric acid, 4-Methyl-2-oxovaleric acid, 3-Methyl-2-oxobutanoic acid, 2-Oxooctanoic acid, Propionic acid, Formic acid, Acetic Acid and combinations thereof. One particular combination contemplated is Propionic acid, Formic acid, and Acetic acid, preferably with an 2:1 ratio of Acetic acid to Formic acid.

In some embodiments, the disclosure relates to the methods of [0010]-[0019], or [0020], wherein the delivery enhancing compound interacts with the nicotine to form particles.

In some embodiments, the disclosure relates to the method of [0021], wherein the particles are less than 6 microns in Mass Median Aerodynamic Diameter.

In some embodiments, the disclosure relates to the method of [0021], wherein the particles are less than 1 micron in Mass Median Aerodynamic Diameter.

In some embodiments, the disclosure relates to the method of [0021], wherein at least some of the particles are between 0.5 and 5 microns in Mass Median Aerodynamic Diameter.

In some embodiments, the disclosure relates to the methods of [0010]-[0023], or [0024], further comprising the step of increasing the temperature of the delivery enhancing compound, the delivery enhancing compound source, the nicotine, the nicotine source and/or the gaseous carrier.

In some embodiments, the disclosure relates to the method of [0025], wherein the temperature is increased to at least 30 degrees Celsius.

In some embodiments, the disclosure relates to the methods of [0010]-[0025], or [0026], wherein the gaseous carrier comprises at least 20 micrograms of nicotine in a volume of gaseous carrier provided to the subject.

In some embodiments, the disclosure relates to the method of [0027], wherein the volume of gaseous carrier delivered to the subject is provided as a single volume.

In some embodiments, the disclosure relates to a method of tobacco product use cessation comprising one or more of the methods of [0010]-[0027], or [0028] and further comprising a delivery to the subject of a therapeutically effective amount of nicotine to at least partially replace nicotine derived from a tobacco product.

In some embodiments, the disclosure relates to a method of treating a disease for which nicotine is therapeutically beneficial comprising one or more of the methods of [0010]-[0027], or [0028], wherein a therapeutically effective amount of nicotine is provided to the subject.

In some embodiments, the disclosure relates to the method of [0030], wherein the disease is selected from the group consisting of nicotine addiction, obesity, Alzheimer's Disease, Parkinson's Disease, Ulcerative Colitis, Multiple Sclerosis, depression, schizophrenia, pain management, ADHD and combinations thereof.

In some embodiments, the disclosure relates to a method of tobacco product substitution comprising delivering nicotine to a subject by the methods of [0010]-[0027], or [0028] to substitute for nicotine derived from a tobacco product.

In some embodiments, the disclosure relates to a method of tobacco product harm reduction comprising delivering nicotine to a subject by the methods of [0010]-[0027], or [0028] to replace nicotine derived from a tobacco product.

In some embodiments, the disclosure relates to a device configured to be capable of carrying out the methods of [0010]-[0032], or [0033].

In some embodiments, the disclosure relates to a device for delivering nicotine to a subject, the device comprising a housing, the housing comprising:

a) an inlet and an outlet in communication with each other and adapted so that a gaseous carrier may pass into the housing through the inlet, through the housing and out of the housing through the outlet, the device comprising in series from inlet to outlet:

b) a first internal area in communication with the inlet, the first internal area comprising a delivery enhancing compound source, c) a second internal area in communication with the first internal area, the second internal area comprising a nicotine source, and d) optionally, a third internal area in communication with the second internal area and the outlet.

In some embodiments, the disclosure relates to the device of [0035] wherein a partial vacuum at the outlet is capable of pulling the gaseous carrier through the inlet, the first compartment, the second compartment, the third compartment, when present, and then through the outlet.

In some embodiments, the disclosure relates to the device of [0035] or [0036] wherein the delivery enhancing compound source comprises an adsorption element with the delivery enhancing compound adsorbed thereon and/or wherein the nicotine source comprises an adsorption element with the nicotine adsorbed thereon.

In some embodiments, the disclosure relates to the device of [0037] wherein the adsorption element or elements comprises at least one of glass, aluminum, Polyethylene Terephthalate (PET), Polybutylene Terephthalate (PBT), Polytetrafluoroethylene (PTFE or TEFLON®), Expanded Polytetrafluoroethylene (ePTFE) (ePTFE is described for example in U.S. Pat. No. 4,830,643), and BARER®.

In some embodiments, the disclosure relates to the devices of [0035]-[0037], or [0038], further comprising a first reservoir in communication with the first internal area, the first reservoir comprising the delivery enhancing compound.

In some embodiments, the disclosure relates to the devices of [0035]-[0038], or [0039], further comprising a second reservoir in communication with the second internal area, the second reservoir comprising nicotine.

In some embodiments, the disclosure relates to the devices of [0035]-[0039], or [0040], comprising the third internal area, the third internal area comprising a third internal area element.

In some embodiments, the disclosure relates to the device of [0041], wherein the third internal area element comprises a purifying agent.

In some embodiments, the disclosure relates to the device of [0042], wherein the purifying agent comprises activated charcoal.

In some embodiments, the disclosure relates to the devices of [0041], [0042], or [0043], wherein the third internal area element comprises a flavoring agent.

In some embodiments, the disclosure relates to the devices of [0041]-[0043], or [0044], where the third internal area element comprises a medicament.

In some embodiments, the disclosure relates to the device of [0045], wherein the medicament comprises nicotine.

In some embodiments, the disclosure relates to the devices of [0035]-[0045], or [0046], wherein the housing simulates a tobacco smoking product.

In some embodiments, the disclosure relates to the device of [0047], wherein the tobacco smoking product is a cigarette.

In some embodiments, the disclosure relates to the devices of [0035]-[0045], or [0046], wherein the housing simulates a pharmaceutical inhalation device.

In some embodiments, the disclosure relates to the device of [0049], wherein the simulated pharmaceutical inhalation device is selected from the group consisting of a metered dose inhaler, a pressurized metered dose inhaler, a dry powder inhaler, a nebulizer, and a liquid based inhaler.

In some embodiments, the disclosure relates to a method of increasing a nicotine concentration in a gaseous carrier comprising a step of placing the gaseous carrier comprising a delivery enhancing compound in communication with a nicotine source comprising the nicotine.

In some embodiments, the disclosure relates to the method of [0051], further comprising the step of placing the gaseous carrier in communication with a delivery enhancing compound source comprising the delivery enhancing compound.

In some embodiments, the disclosure relates to the method of [0052], wherein the step of placing the gaseous carrier in communication with the delivery enhancing compound source precedes the step of placing the gaseous carrier comprising the delivery enhancing compound in communication with the nicotine source.

In some embodiments, the disclosure relates to the method of [0051], [0052], or [0053], wherein the delivery enhancing compound source comprises a plurality of compartments comprising two or more precursor compounds.

In some embodiments, the disclosure relates to the method of [0054], wherein the delivery enhancing compound comprises ammonium chloride and the two or more precursor compounds include ammonia and hydrogen chloride.

In some embodiments, the disclosure relates to the method of [0051]-[0054], or [0055], wherein the nicotine concentration in the gaseous carrier is increased relative to the nicotine concentration that would be contained in the gaseous carrier without the delivery enhancing compound.

In some embodiments, the disclosure relates to the method of [0051]-[0055], or [0056], wherein the delivery enhancing compound comprises an acid.

In some embodiments, the disclosure relates to the method of [0057], wherein the acid is an organic acid.

In some embodiments, the disclosure relates to the method of [0058], wherein the organic acid has a greater vapor pressure than nicotine at a given temperature.

In some embodiments, the disclosure relates to the method of [0059], wherein the given temperature is 25, 30, 40, 45, 70 or 100 degrees Celsius.

In some embodiments, the disclosure relates to the method of [0057], wherein the acid is selected from the group consisting of 3-Methyl-2-oxovaleric acid, Pyruvic acid, 2-Oxovaleric acid, 4-Methyl-2-oxovaleric acid, 3-Methyl-2-oxobutanoic acid, 2-Oxooctanoic acid, Propionic acid, Formic acid, Acetic Acid and combinations thereof. One particular combination contemplated is Propionic acid, Formic acid, and Acetic acid, preferably with an 2:1 ratio of Acetic acid to Formic acid.

In some embodiments, the disclosure relates to the method of [0051]-[0060], or [0061], wherein the delivery enhancing compound interacts with the nicotine to form particles.

In some embodiments, the disclosure relates to the method of [0062], wherein some or all of the particles are less than 6 microns in Mass Median Aerodynamic Diameter.

In some embodiments, the disclosure relates to the method of [0062], wherein some or all of the particles are less than 1 micron in Mass Median Aerodynamic Diameter.

In some embodiments, the disclosure relates to the method of [0062], wherein at least some of the particles are between 0.5 and 5 microns in Mass Median Aerodynamic Diameter.

In some embodiments, the disclosure relates to the method of [0051]-[0064], or [0065], further comprising the step of increasing the temperature of the delivery enhancing compound, the delivery enhancing compound source, the nicotine, the nicotine source and/or the gaseous carrier.

In some embodiments, the disclosure relates to the method of [0066], wherein the temperature is increased to at least 30 degrees Celsius.

In some embodiments, the disclosure relates to the method of [0067], wherein the temperature is elevated by a plurality of heating steps.

In some embodiments, the disclosure relates to a nicotine for tobacco product use cessation, the nicotine delivered by the method of [0051]-[0067], or [0068], further comprising the step of providing the gaseous carrier to a subject after the step of placing the gaseous carrier comprising the delivery enhancing compound in communication with the nicotine source.

In some embodiments, the disclosure relates to the nicotine of [0069], wherein the gaseous carrier comprises at least 20 micrograms of nicotine in a volume of gaseous carrier provided to the subject.

In some embodiments, the disclosure relates to the nicotine of [0070], wherein the volume of gaseous carrier delivered to the subject is provided as a single volume.

In some embodiments, the disclosure relates to a nicotine for tobacco product harm reduction, the nicotine delivered by the method of [0051]-[0067], or [0068], further comprising the step of providing the gaseous carrier to a subject after the step of placing the gaseous carrier comprising the delivery enhancing compound in communication with the nicotine source.

In some embodiments, the disclosure relates to the nicotine of [0072], wherein the gaseous carrier comprises at least 20 micrograms of nicotine in a volume of gaseous carrier provided to the subject.

In some embodiments, the disclosure relates to the nicotine of [0073], wherein the volume of gaseous carrier delivered to the subject is provided as a single volume.

In some embodiments, the disclosure relates to a nicotine for tobacco product substitution, the nicotine delivered by the method of [0051]-[0067], or [0068], further comprising the step of providing the gaseous carrier to a subject after the step of placing the gaseous carrier comprising the delivery enhancing compound in communication with the nicotine source.

In some embodiments, the disclosure relates to the nicotine of [0075], wherein the gaseous carrier comprises at least 20 micrograms of nicotine in a volume of gaseous carrier provided to the subject.

In some embodiments, the disclosure relates to the nicotine of [0076], wherein the volume of gaseous carrier delivered to the subject is provided as a single volume.

In some embodiments, the disclosure relates to a nicotine for the treatment of a disease selected from the group consisting of nicotine addiction, obesity, Alzheimer's Disease, Parkinson's Disease, Ulcerative Colitis, Multiple Sclerosis, depression, schizophrenia, pain management, ADHD and combinations thereof, the nicotine delivered by the method of [0051]-[0067], or [0068], further comprising the step of providing the gaseous carrier to a subject after the step of placing the gaseous carrier comprising the delivery enhancing compound in communication with the nicotine source.

In some embodiments, the disclosure relates to a device configured to be capable of carrying out a) the method of [0051]-[0067], or [0068]; and/or b) configured to be capable of delivering the nicotine of [0069]-[0077], or [0078].

In some embodiments, the disclosure relates to a use of nicotine for the manufacture of a medicament for delivery by the method of [0051]-[0067], or [0068].

In some embodiments, the disclosure relates to a use of nicotine for the manufacture of a medicament for tobacco product use cessation for delivery by the method of [0051]-[0067], or [0068].

In some embodiments, the disclosure relates to a use of nicotine for the manufacture of a medicament for tobacco product harm reduction for delivery by the method of [0051]-[0067], or [0068].

In some embodiments, the disclosure relates to a use of nicotine for the manufacture of a medicament for tobacco product substitution for delivery by the method of [0051]-[0067], or [0068].

In some embodiments, the disclosure relates to a use of nicotine for the manufacture of a medicament for the treatment of a disease selected from the group consisting of nicotine addiction, obesity, Alzheimer's Disease, Parkinson's Disease, Ulcerative Colitis, Multiple Sclerosis, depression, schizophrenia, pain management, ADHD and combinations thereof, the nicotine delivered by the method of [0051]-[0067], or [0068], further comprising the step of providing the gaseous carrier to a subject after the step of placing the gaseous carrier comprising the delivery enhancing compound in communication with the nicotine source.

In some embodiments, the disclosure relates to a method for delivering a medicament to a user, the method comprising:
passing a gaseous stream over a first substance to create a first vapor-containing gaseous stream;
passing the first vapor-containing gaseous stream over a second substance to create particles in the gaseous stream; and
delivering the gaseous stream containing the particles to a user.

In some embodiments, the disclosure relates to the method of [0085], wherein the step of creating the first vapor-containing gaseous stream comprises capturing a vapor of the first substance in the gaseous stream.

In some embodiments, the disclosure relates to the method of [0085] or [0086], wherein the step of creating particles comprises contacting a vapor of the second substance with the first vapor-containing gaseous stream.

In some embodiments, the disclosure relates to the method of [0085], [0086], or [0087], wherein the step of creating the particles comprises an interaction between the first and second substances.

In some embodiments, the disclosure relates to the method of [0088], where said interaction comprises an acid-base reaction.

In some embodiments, the disclosure relates to the method of [0085]-[0088], or [0089], where the first and second substances are volatile substances.

In some embodiments, the disclosure relates to the method of [0090], wherein the first substance is more volatile at ambient temperature than the second substance.

In some embodiments, the disclosure relates to the method of [0085]-[0090], or [0091], wherein one of the first substance and/or the second substance comprises a nicotine.

In some embodiments, the disclosure relates to the method of [0092], wherein the nicotine comprises free base nicotine.

In some embodiments, the disclosure relates to the method of [0085]-[0092], or [0093], wherein the particles comprise nicotine-containing particles.

In some embodiments, the disclosure relates to the method of [0085]-[0093], or [0094], wherein the gaseous stream delivered to a user contains more than 20 micrograms of nicotine-containing particles.

In some embodiments, the disclosure relates to the method of [0085]-[0094], or [0095], wherein the particles comprise nicotine salt particles.

In some embodiments, the disclosure relates to the method of [0085]-[0095], or [0096], wherein the first substance comprises an acid.

In some embodiments, the disclosure relates to the method of [0097], wherein the acid comprises pyruvic acid.

In some embodiments, the disclosure relates to the method of [0085]-[0097], or [0098], wherein the particles comprise nicotine pyruvate.

In some embodiments, the disclosure relates to the method of [0097], wherein the acid comprises 3-methyl-2-oxobutanoic acid.

In some embodiments, the disclosure relates to the method of [0085]-[0099], or [0100], wherein the particles comprise nicotine 3-methyl-2-oxobutanoate.

In some embodiments, the disclosure relates to the method of [0085]-[0100], or [0101], wherein at least some of the particles are visible particles.

In some embodiments, the disclosure relates to the method of [0085]-[0101], or [0102], wherein at least some of the particles are delivered to the lungs of the user.

In some embodiments, the disclosure relates to the method of [0085]-[0102], or [0103], wherein the particles are less than 6 microns in diameter.

In some embodiments, the disclosure relates to the method of [0085]-[0103], or [0104], wherein at least some of the particles are between 0.5 and 5 microns in diameter.

In some embodiments, the disclosure relates to the method of [0010]-[0027], or [0028]; or the method of [0051]-[0067], or [0068]; or the use of [0080] wherein a medicament listed at [0132], such as a compound identified by numbers 1-70 in [0132], is used instead, of or in addition to, the nicotine recited in [0010]-[0027], or [0028]; [0051]-[0067], or [0068]; or [0080].

In some embodiments, the disclosure relates to the device of [0035]-[0049], or [0050] wherein the device is adapted to deliver a medicament listed at [0132], such as a compound identified by numbers 1-70 in [0132], instead of, or in addition to, the nicotine.

In some embodiments, the disclosure relates to use of a medicament of [0132], such as a compound identified by numbers 1-70 in [0132], for delivery by the methods of [0010]-[0027], or [0028]; or [0051]-[0067], or [0068] for treatment of a disease for which the medicament is therapeutically beneficial.

Improved Nicotine Source

In some embodiments, the disclosure relates to a method of [0010]-[0032], or [0033]; [0051]-[0067], or [0068]; [0069]-[0077], or [0078]; [0080]-[0083], or [0084]; or a device listed above for carrying out the method, wherein the nicotine source comprises the nicotine and an electrolyte forming compound, both in an aqueous solution.

In some embodiments, the electrolyte forming compound of the method of [0110] is an Alkali metal hydroxide or oxide; or an Alkaline earth metal oxide; or a salt (including bases) or selected from the group consisting of the compounds listed in Table 11 of [0374] such as the bases sodium hydroxide (NaOH), calcium hydroxide (Ca(OH)$_2$), and potassium hydroxide (KOH) and combinations thereof.

In some embodiments, the nicotine of the method of [0110] or [0111] is selected from nicotine base and a nicotine salt such as nicotine-HCl, nicotine-bitartrate, nicotine-ditartrate and combinations thereof.

In some embodiments, the nicotine of the method of [0110], [0111] or [0112] is selected from nicotine base and nicotine bitartrate and combinations thereof and the electrolyte forming compound is selected from the group consisting of sodium hydroxide (NaOH), calcium hydroxide (Ca(OH)$_2$), and potassium hydroxide (KOH) and combinations thereof.

In some embodiments, the nicotine of the method of [0110], [0111] or [0112] is selected from nicotine base and nicotine bitartrate and combinations thereof and the electrolyte forming compound comprises KOH.

In some embodiments of the method of [0110]-[0113] or [0114], the pH of the aqueous solution is equal to or greater than 9.0 such as equal to or greater than pH 10, 11, 12, 13 or 14.

In embodiments of the method of [0110]-[0114] or [0115], wherein the electrolyte forming compound is KOH, the ratio of KOH to nicotine base (or base equivalents) is 10:40, 10:60, 10:80 or 10:100 with 10:60 preferred. These points also form the boundaries of various exemplary ranges within the present invention such as the range 10:40 to 10:100.

In some embodiments of the method of [0110]-[0113] or [0114], the method further comprises the step of mixing the electrolyte forming compound with the nicotine in an aqueous solution.

In some embodiments of the method of [0117], the electrolyte forming compound is exothermic when dissolved into the aqueous solution, and is preferably added in sufficient amount to elevate the temperature of the aqueous solution of nicotine, such as to about 80 degrees C. or higher.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF DRAWINGS

For a more complete understanding of the present invention, reference is now made to the following descriptions taken in conjunction with the accompanying drawing, in which.

DETAILED DESCRIPTION

Figure 1:
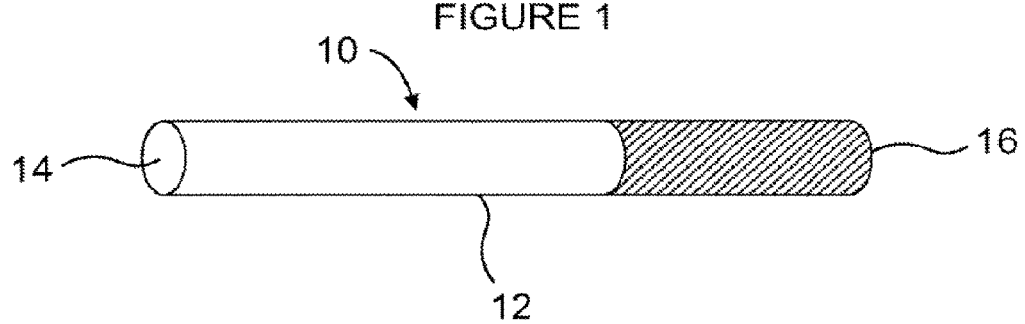
FIG. 1 a perspective view of the exterior of an exemplary delivery device simulating a cigarette.

"Particle" as used herein may refer to a liquid droplet, a solid particulate or a combination of both such as a liquid droplet nucleated by a solid particulate.

"Therapeutically effective amount" as used herein may refer to a concentration or amount of nicotine or other medicament which achieves a therapeutic effect in a subject, generally a human subject. The subject has an improvement in a disease or medically defined condition. The improvement is any improvement or remediation of the symptoms associated with the disease. The improvement is an observable or measurable improvement. Thus, one of skill in the art realizes that a treatment may improve the disease condition, but may not be a complete cure for the disease. The therapeutic effect in some embodiments may include reduction or elimination of nicotine craving in a subject suffering nicotine addiction or in a subject experiencing nicotine use withdrawal symptoms.

"Electrolyte forming compound" as used herein may refer to a neutral or ionic substance that dissociates into ions in solution.

To aid in the understanding of the concepts of the present invention, embodiments will be described herein with reference to devices and methods for nicotine delivery. It will be appreciated by one of ordinary skill in the art that the medicaments listed at [0132] may be used in place of or in addition to the nicotine according to the teachings herein.

The methods described herein relate to a surprising discovery regarding the dose of nicotine obtained from nicotine delivery devices. The inventors have unexpectedly identified methods for increasing the dose of nicotine delivered to a subject by inhalation. The importance of this discovery lies in an improved ability to substitute for the nicotine delivery subjects experience while smoking cigarettes and similar tobacco products. With improved nicotine delivery profiles, subjects applying the methods described herein will be provided with superior nicotine replacement therapy during attempts at smoking cessation, harm reduction and/or substitution. With the continued global problem of smoking related health issues, the methods described herein address a critical need in medical efforts to assist smokers in quitting.

Without desiring to be bound by theory, it is believed that passing the vapor of a volatile first substance (i.e. a delivery enhancing compound) over a nicotine source results in the formation of particles in a liquid or solid state, which subsequently allows more of the nicotine to evaporate and combine with the first substance, generating further particles. The amount of particle formation (mass delivered) at a given temperature would be greater than that formed when the vapor of nicotine is passed over a second volatile substance. Similarly, the amount of particle formation at a given temperature would be greater than that formed when the vapors of the two substances are combined in a parallel mixing apparatus (as disclosed in prior art), due to the amount of particle formation being limited by the volatility of the less volatile substance and to the dilution of the active substance by mixing with the volume of gas containing the other substance. Also, allowing sequential passing of one substance over a second substance may allow for a more efficient combination of the two substances than parallel mixing as disclosed in prior art. Another possibility is that the interaction between the first and second substances is an exothermic process. In other words, energy is released in the form of heat as a result of the exothermic interaction. Without desiring to be bound by theory, it is believed that the heat released may enhance the evaporation of the nicotine.

In some embodiments, the methods involve the step of bringing a gaseous carrier in communication with a nicotine source. The gaseous carrier in these embodiments contains a delivery enhancing compound capable of increasing the amount of nicotine in the gaseous carrier, relative to the amount of nicotine that would be in the gaseous carrier lacking the delivery enhancing compound. In some embodiments, the delivery enhancing compound is capable of reacting with nicotine base or other medicament to form a salt. In particular embodiments, the delivery enhancing compound is capable of reacting with nicotine base to form salt particles. In preferred embodiments, the particles are less than 6 micrometers, more preferably less than 1 micrometer, in Mass Median Aerodynamic Diameter. (For Mass Median Aerodynamic Diameter determinations, see Katz I M, Schroeter J D, Martonen T B, Factors affecting the deposition of aerosolized insulin, *Diabetes technology & Therapeutics*, vol. 3 (3), 2001, pp 387-397, incorporated by reference for this teaching).

The methods disclosed herein may be adapted for use with a variety of other medicaments having similar biophysical and/or chemical properties to nicotine. The following compounds are aliphatic or aromatic, saturated or unsaturated nitrogenous bases (nitrogen containing hydrogen ion or Lewis acid accepting compounds) in which a nitrogen atom is present in a heterocyclic ring or in an acyclic chain (substitution). In addition, the compounds have been selected based on melting point (below 150° C.) or boiling point (below 300° C.) that are expected to favor volatilization:

| | Medicaments Other than Nicotine |
|---|---|
| 1. | 7-Hydroxymitragynine |
| 2. | Amphetamine |
| 3. | Arecoline |
| 4. | Atropine |
| 5. | Bupropion |
| 6. | Cathine (D-norpseudoephedrine) |
| 7. | Cathinone (β-ketoamphetamine) |
| 8. | Chlorpheneramine |
| 9. | Dibucaine |
| 10. | Dimemorphan |
| 11. | Dimethyltryptamine |
| 12. | Diphenhydramine |
| 13. | Ephedrine |
| 14. | Hordenine |
| 15. | Hyoscyamine |
| 16. | Isoarecoline |
| 17. | Levorphanol |
| 18. | Lobeline |
| 19. | Mescaline |
| 20. | Mesembrine |
| 21. | Mitragynine |
| 22. | Muscarine |
| 23. | Parahydroxyamphetamine |
| 24. | Procaine |
| 25. | Pseudo ephedrine |
| 26. | Pyrilamine |
| 27. | Raclopride |
| 28. | Ritodrine |
| 29. | Scopolamine |
| 30. | Sparteine (Lupinidine) |
| 31. | Ticlopidine |
| | Tobacco Smoke Constituents: |
| 32. | 1,2,3,4-Tetrahydroisoquinolines |
| 33. | Anabasine |
| 34. | Anatabine |
| 35. | Cotinine |
| 36. | Myosmine |
| 37. | Nicotrine |
| 38. | Norcotinine |
| 39. | Nornicotine |
| | Anti-asthmatic drugs |
| 40. | Orciprenaline |
| 41. | Propranolol |
| 42. | Terbutaline |
| | Anti-angina drugs |
| 43. | Nicorandil |
| 44. | Oxprenolol |
| 45. | Verapamil |

-continued

| | Antiarrhythmic drugs |
|---|---|
| 46. | Lidocaine |
| | Nicotinic receptor agents |
| | A. Nicotinic agonist |
| 47. | Epibatidine |
| 48. | 5-(2R)-azetidinylmethoxy)-2-chloropyridine (ABT-594) |
| 49. | (S)-3-methyl-5-(1-methyl-2-pyrrolidinyl)isoxazole (ABT 418) |
| 50. | (±)-2-(3-Pyridinyl)-1-azabicyclo[2.2.2]octane (RJR-2429) |
| | B. Nicotinic antagonist: |
| 51. | Methyllycacotinine |
| 52. | Mecamylamine |
| | C. Acetyl cholinesterase inhibitors |
| 53. | Galantamine |
| 54. | Pyridostigmine |
| 55. | Physostigmine |
| 56. | Tacrine |
| | MAO-inhibitors |
| 57. | 5-Methoxy-N,N-dimethyltryptamine |
| 58. | 5-methoxy-α-methyltryptamine |
| 59. | Alpha-methyltryptamine |
| 60. | Iproclozide |
| 61. | Iproniazide |
| 62. | Isocarboxazide |
| 63. | Linezolid |
| 64. | Meclobemide |
| 65. | N,N-Dimethyltryptamine |
| 66. | Phenelzine |
| 67. | Phenyl ethylamine |
| 68. | Toloxatone |
| 69. | Tranylcypromine |
| 70. | Tryptamine |

Gaseous Carrier and Source Thereof

The gaseous carrier may be any gas capable of containing nicotine base and the delivery enhancing compound. One of skill in the art will readily be able to select an appropriate gaseous carrier based on the intended use, form of nicotine and specific delivery enhancing compound(s). In preferred embodiments, the gaseous carrier is substantially inert with regard to the form of nicotine and/or the delivery enhancing compound carried, at least for the time period contemplated for delivery to a subject. In some embodiments, the gaseous carrier is ambient air. In other embodiments the gaseous carrier is a substantially pure gas such as carbon dioxide or nitrogen gas, or a blend of such gases. In such embodiments, the gaseous carrier is supplied from a container designed to hold and deliver the gaseous carrier in a manner to effect the methods described herein. For example, in embodiments using metered dose inhaler devices, the gaseous carrier may comprise Hydrofluorocarbons, which include Hydrofluoroalkanes (HFAs) as propellants. In some of these embodiments, the HFAs, are one or more of HFA 134a and HFA 227.

Delivery Enhancing Compounds

Delivery enhancing compounds are those compounds capable of increasing the total concentration of nicotine in a gaseous carrier when the gaseous carrier is placed in communication with a nicotine source. Nicotine has a vapor pressure of 0.04 mm Hg at 25° C. Delivery enhancing compounds having a vapor pressure greater than nicotine at a given temperature are preferred if ambient temperatures are used. Non-limiting examples include inorganic acids such as hydrochloric, hydrobromic, or sulfuric acid, and organic acids including saturated and unsaturated aliphatic acids, saturated and unsaturated alicyclic acids, aromatic acids (including heterocyclic aromatic), polycarboxylic acids, hydroxy, alkoxy, keto, and oxo acids, thioacids, amino acids, and each of the preceding optionally substituted with one or more heteroatoms, including but not limited to halogens. In some embodiments, the delivery enhancing compound is a carboxylic acid. In some of these embodiments, the carboxylic acid is in the class termed "2-Oxo acids." In some of these embodiments, the carboxylic acid is in the class of α-Keto acids known as "2-Keto acids." In some of these embodiments, the acid is selected from the group consisting of 3-Methyl-2-oxovaleric acid, Pyruvic acid, 2-Oxovaleric acid, 4-Methyl-2-oxovaleric acid, 3-Methyl-2-oxobutanoic acid, 2-Oxooctanoic acid and combinations thereof. In some embodiments, the delivery enhancing compound forms solid particles, for example salt particles. In other embodiments, the delivery enhancing compound forms a liquid droplet aerosol.

Alternatively, the delivery enhancing compound forms a particulate aerosol, the particles of which may, for example, adsorb or absorb nicotine base. In particular embodiments, the particulate aerosol includes ammonium chloride salt particles. In embodiments comprising nicotine particle formation or nicotine adsorption/absorption onto particles the particles formed are preferably less than 6 microns, more preferably less than 5 microns or less than 1 micron in size.

Nicotine (or Other Medicament) Sources

Embodiments of a nicotine source use a compound comprising any chemical capable of providing a volatile form of nicotine such as nicotine base or nicotine salts (e.g. nicotine-HCl, -bitartrate, -ditartrate). Although more than one form of nicotine can be used, free base nicotine is preferred. The nicotine source may comprise other compounds such as antioxidants (e.g., BHA, BHT, and ascorbate) for stabilizing the nicotine. In some embodiments, nicotine is adsorbed on an element to provide a nicotine source. The adsorbed nicotine is held on the surface of a relatively inert material. Non-limiting examples of adsorption element materials include glass, stainless steel, aluminum, PET, PBT, PTFE, ePTFE, and BAREX®. Adsorption is a process that occurs when a gas, liquid or solid solute accumulates on the surface of a solid or, more rarely, a liquid (adsorbent), forming a molecular or atomic film (the adsorbate). Physical adsorption is typically the result of van der Waals forces and electrostatic forces between adsorbate molecules and the atoms which compose the adsorbent surface. Thus adsorbents are characterized by surface properties such as surface area and polarity.

A large specific surface area is preferable for providing large adsorption capacity, but the creation of a large internal surface area in a limited volume inevitably gives rise to large numbers of small sized pores between adsorption surfaces. The size of the micropores determines the accessibility of adsorbate molecules to the internal adsorption surface, so the pore size distribution of micropores is another important property for characterizing adsorptivity of adsorbents. Surface polarity corresponds to affinity with polar substances such as water or alcohols. Polar adsorbents are thus called "hydrophilic" and aluminosilicates such as zeolites, porous alumina, silica gel or silica-alumina are examples of adsorbents of this type. On the other hand, non-polar adsorbents are generally "hydrophobic." Carbonaceous adsorbents, polymer adsorbents and silicalite are typical non-polar adsorbents. These adsorbents have more affinity with oil or hydrocarbons than water. In some embodiments, the adsorbing surface also wicks the adsorbed material by capillary action, when the adsorbent is in liquid form. Wicking occurs when the adhesive intermolecular forces between the liquid and an adsorbing surface are stronger than the cohesive intermolecular forces inside the liquid. The effect causes a concave meniscus to form where the substance is touching a vertical adsorbing surface. Adsorbing surfaces may be selected or designed to wick hydrophilic or hydrophobic liquids.

In alternative embodiments, the nicotine source element can comprise an absorbing (either porous or nonporous) material. Non-limiting examples of nicotine source element materials include polyethylene (PE) and polypropylene (PP).

A nicotine source may in some embodiments be or be in communication with a nicotine reservoir. In some embodiments, the reservoir contains a volume of nicotine in liquid form with the liquid reservoir in communication with an adsorbing or absorbing nicotine source element. In other embodiments, the nicotine reservoir is or forms part of the nicotine source element. A non-limiting example of such a combination source and reservoir would be a material (e.g., PE or PP) saturated with nicotine solution. In particular embodiments, the reservoir provides sufficient nicotine solution to enable a delivery device to provide therapeutically effective doses of nicotine over a desired time frame. Non-limiting examples would be devices capable of delivering 0-100 micrograms of nicotine per 35 cubic centimeter volume "puff" of gaseous carrier for a desired number of puffs per day (e.g., 200) over a desired number of days (e.g., 1-7 days). In certain embodiments, the amount of nicotine delivered is between 10 and 110, 20 and 100, 50 and 100, or 40 and 60 micrograms of nicotine per 35 cubic centimeter volume "puff."

Other medicaments listed at [0132] may be used in place of or in addition to nicotine to form sources of medicament(s) using the same principles applied to nicotine base as the example species above.

Improved Nicotine Source

In the embodiments of the predecessor to this improvement application wherein nicotine was the medicament, nicotine delivery was reduced to undesirably low levels after a certain number of puffs while significant amounts of nicotine remained in the prior devices. The fall off profile of nicotine delivery was countered by the inclusion of more nicotine. However this larger amount of nicotine left an even larger residue of nicotine in the nicotine source, after the aerosol delivery fell below useful levels. While the prior art devices worked well to deliver nicotine for therapeutic effect, these limitations, a) the amount of nicotine required and b) the residual nicotine content after use, posed problems in designing an efficient aerosol device for commercial production. For example, significant residual nicotine in a device could trigger regulatory approval problems in some countries.

Per the predecessor application, one method to increase the efficiency of nicotine use and extend the useful delivery profile over more puffs per unit of nicotine content is to apply heat. When we applied heat to the nicotine base, the nicotine delivery was dramatically increased and also the number of puffs having useful nicotine delivery levels was increased. Hence, we concluded that application of heat to the nicotine base was useful for enhancing the nicotine aerosol delivery and also helped to diminish the rate of the nicotine concentration fall off per puff over time. However, our goal was to avoid the use of heating elements in the device to enhance the nicotine delivery as this technology would increase the cost of production which will be eventually passed to the consumer, and might also make the pathway to regulatory approval more difficult.

We thus sought alternatives to heating to increase the efficiency of delivery and to reduce the amount of residual nicotine in a, device after use was complete. In experimenting with nicotine sources, we unexpectedly discovered that the addition of electrolyte forming compounds to nicotine salts or nicotine base in water/nicotine solutions resulted in dramatic improvements in both delivery and reduced residual nicotine relative to aqueous nicotine solutions without electrolyte forming compounds and as compared to nicotine base without added electrolyte forming compounds. Exemplary electrolyte forming compounds may be found in Table 11 below and include strong bases such as sodium hydroxide (NaOH) and potassium hydroxide (KOH), with KOH particularly preferred. Preferred forms of nicotine for use in the improved source are nicotine base and/or nicotine bitartrate. An especially preferred combination is nicotine base and KOH in water. These improved nicotine plus electrolyte forming compound formulations are fully compatible with the devices and compositions of the predecessor application. The dramatic and surprising improvements seen with these modified nicotine sources are demonstrated in the additional Improvement Experiments #1-6 and Designs #1-3 below.

Delivery Enhancing Compound Sources

In some embodiments of the methods, the gaseous carrier is provided pre-combined with the delivery enhancing compound. Other embodiments of the methods described herein include a step of loading gaseous carrier with a delivery enhancing compound prior to or concurrently with passage of the gaseous carrier over the nicotine source. In embodiments encompassing a step of loading gaseous carrier with a delivery enhancing compound, the delivery enhancing compound is generally provided in the form of a delivery enhancing compound source. The gaseous carrier in these embodiments is generally brought into direct communication with the delivery enhancing compound source such that the delivery enhancing compound may enter the gaseous carrier from the delivery enhancing compound source. In some embodiments, a delivery enhancing compound source comprises a delivery enhancing compound source element containing materials which adsorb or absorb the delivery enhancing compound. Delivery enhancing compound source element materials will generally be inert with respect to the delivery enhancing compound. In some embodiments, the delivery enhancing compound is an acid as described above. Non-limiting examples of adsorption element materials for such embodiments include glass, stainless steel, aluminum, PET, PBT, PTFE, ePTFE, and BAREX®. Non-limiting examples of absorption element materials for such embodiments include PE and PP.

A delivery enhancing compound source may in some embodiments be, or be in communication with, a delivery enhancing compound reservoir. In some embodiments, the reservoir contains a volume of delivery enhancing compound in liquid form with the liquid reservoir in communication with an adsorbing or absorbing delivery enhancing compound source element. In other embodiments, the nicotine reservoir is or forms part of the delivery enhancing compound source element. A non-limiting example of such a combination source and reservoir would be a material (e.g., PE or PP) saturated with delivery enhancing compound solution. In particular embodiments, the reservoir provides sufficient delivery enhancing compound solution to enable a delivery device to provide therapeutically effective doses of nicotine over a desired time frame. Non-limiting examples would be devices capable of delivering sufficient delivery enhancing compound to enable delivery of 0-100 micrograms of nicotine per 35 cubic centimeter volume "puff" of gaseous carrier for a desired number of puffs per day (e.g. 200) over a desired number of days (e.g. 1-7 days). In certain embodiments, the amount of nicotine delivered is between 10 and 110, 20 and 100, 50 and 100, or 40 and 60 micrograms of nicotine per 35 cubic centimeter volume "puff." Embodiments delivering 0 micrograms of nicotine are generally intended to be the end points of a gradual nicotine reduction based, tobacco product cessation program.

Temperature

In some embodiments of the methods, the method involves a step of increasing the temperature of one or more of the gaseous carrier, the nicotine source and/or the enhancer source (when present). Such temperature control steps are generally used to regulate or to further enhance the amount of nicotine delivery. In some embodiments, the increase in temperature is used only if the nicotine levels delivered would generally be otherwise expected to drop below a desired minimum. In some embodiments this may be more than 20 micrograms, preferably more than 30 micrograms, and more preferably more than 40 micrograms of nicotine per 35 cc volume puff. For example, a common target delivery concentration is 40-50 micrograms nicotine per 35 cubic centimeter volume "puff" as measured by a well known technique in the nicotine delivery field. See The FTC Cigarette Test Method for Determining Tar, Nicotine and Carbon Monoxide Yield of U.S. Cigarettes: Report of the NCI Ad Hoc Committee. Smoking and Tobacco Control Monograph #7. Dr. R. Shopland (Ed.). Darby, Pa.: Diane Publishing Co, 1996. In some embodiments, generally a lower temperature is used first with the temperature increasing over time to sustain a desired nicotine delivery concentration from a nicotine source. In other embodiments a constant temperature is maintained during use. In some embodiments, the temperature is elevated to a maximum of 100 degrees C., a maximum of 70 degrees C., or the temperature is elevated to 40±5 degrees C. For example, pyruvic acid as a delivery enhancing compound may be heated to 40 degrees C. to facilitate sustained nicotine delivery over multiple puffs at a desired nicotine concentration range (e.g. 20-50 micrograms per puff). Temperature control may in some embodiments be effected by a temperature control element. Such elements may be any known mechanism capable of achieving the desired target temperature for the gaseous carrier, the nicotine and/or the delivery enhancing compound(s). Particular examples of temperature control elements are illustrated below in the exemplary devices provided. Alternatively, exothermic chemical heat may be employed to enhance nicotine delivery. For example, base compounds may be mixed with the nicotine and/or water at the time of aerosol formation to generate exothermic heat and thereby increase the efficiency of nicotine use and sustain nicotine delivery over an increased number of puffs relative to aerosol formation at room temperature. The exothermic reaction can be separate from the nicotine source for example a water-KOH mixture to produce just heat for increased temperature. The base may also be admixed with the nicotine of the nicotine source, with or without water but preferably with water, to both generate heat and further enhance nicotine delivery as discussed for the improved nicotine source. In either case, the exothermic heat may be harnessed to raise the temperature of any component of a delivery device, such as one or more of the gaseous carrier, the nicotine source and/or the enhancer source (when present); and other components such as flavoring compounds for rendering the nicotine/gaseous carrier more palatable for inhalation.

Devices

The methods described herein are generally carried out using specially adapted delivery devices configured to carry out the methods described herein during device operation. One of skill in the art will be able to design and produce a variety of delivery devices using the foregoing guidance. The Inventors however provide herein a number of delivery device configurations to further illustrate the methods herein and their practical application by way of specific examples. The gaseous carrier delivered to a device user can include a therapeutically effective dose of nicotine for smoking cessation, harm reduction and/or substitution. Preferred delivery device embodiments are pulmonary delivery systems. Pulmonary delivery systems have the ability to deliver consistent doses with suitable particle-size and low particle-size variability, to the deep lung. The advantages of pulmonary drug delivery are not limited to needle-free dosing and its attendant improvements in patient acceptance and compliance. Of the various non-invasive drug delivery technologies available, including nasal, transdermal, buccal, and needle-free injections, pulmonary delivery offers unique potential for precise dose titration, rapid absorption, and high bioavailability to deliver novel therapeutics and improve delivery of existing compounds.

MODES FOR CARRYING OUT THE INVENTION

Screening for a Suitable Experimental Design for Nicotine Aerosol Formation

Several experimental designs were tested as described below to evaluate the generation of aerosol particles by allowing acid vapor to react instantly with base vapor.

Experiment #1: Hydrochloric Acid and Ammonia were Used to Generate a Mixture of Vapors in a "Y" Shaped Tube that was then Passed Over Nicotine Free Base Objective:

The aim was to evaluate the effectiveness of a chemically robust acid/base system to generate an aerosol of sufficient characteristics to aerosolize nicotine free base.

Experimental Design:

The experimental design included two identical glass test tubes (Tube A contained 5 ml of hydrochloric acid (HCl) and Tube B contained 5 ml ammonia ($NH_3$)) connected through a "Y" shape tube designed to allow for the vapors from the two test tubes to be admixed instantly in the "Y" shape tubing and then passed over nicotine free base using a Controlled Puff Volume Apparatus, CPVA (40 cc air at 2 seconds' duration (3-second interval) for 100 times (100 puffs)). The admixture of HCl and $NH_3$ vapors produced a white, dense and visible cloud.

Results:

TABLE 1

Amount of Nicotine Obtained After Passing HCl and NH₃ Over Nicotine

| Sample ID | Nicotine (µg)/sample | Nicotine (µg)/puff |
|---|---|---|
| HCl and NH₃ only | 0 | 0 |
| Nicotine, HCl and NH₃ | 3796.2 | 37.9 |
| Nicotine only | 1291.9 | 12.9 |

Discussion:

The use of hydrochloric acid, ammonia and nicotine resulted in significant nicotine delivery vs. nicotine only, as shown in Table 1. However, due to the chemical reactivity and corrosive nature of the acid and base chosen for this experiment, alternative constituents were evaluated that are more amenable to human use such as non-corrosive acid alternatives, including volatile and low-volatility organic acids (e.g., fatty acids).

Experiment #2: Screening for Suitable Acid Candidates for Use in the Development of Acid Over Nicotine Base Aerosol Delivery Arrangement Objective:

The objective of this experiment was to evaluate a series of acid candidates for their ability to admix with nicotine free base to form an aerosol suitable for pulmonary delivery. The superior candidates which created aerosols containing the greatest mass of nicotine free base reported as µg/puff were selected for further evaluation. Volatile carboxylic acids were selected as the organic acid of choice due to their relative high volatility and to the fact that they are constituents of cigarettes and other commercial products for human consumption such as food additives, flavoring agents and sweetening agents.

Experimental Design:

Two identical rectangular glass chambers measuring 4 cm×2 cm×1 cm each contained two inlet/outlet ports extending externally through the top of the chamber before turning 90° away from the center of the chamber. These ports were positioned on opposite sides and near the edge of the chambers. Internally, these ports consisted of a hollow glass tube that extends to near the bottom of the chamber. The purpose of these ports is to provide a controlled pathway for the movement of air across a volume of nicotine free base (chamber "B") or candidate acid (chamber "A"). For this experiment chamber B was filled with 200 µL nicotine free base and chamber A was filled with 200 µL pyruvic acid. The volumes of nicotine free base and pyruvic acid were added by Eppendorf pipette. Neat nicotine free base and neat pyruvic acid was stored at 4° C. and under Nitrogen gas. The working volumes of the nicotine free base and pyruvic acid were stored under refrigerated conditions but not under nitrogen. The working volumes were brought to room temperature before transferring to the chambers. A temperature probe was used to verify that the working volumes had reached room temperature. A filling portal was crafted into each chamber and positioned on the top center panel and was used for filling the chambers with the appropriate reactants. Once the appropriate volume was added to the individual chamber, the portal was sealed using a plug of PARAFILM® that was outer layered with TEFLON® tape. The chambers were then connected sequentially using TEFLON® tubing, secured by PARAFILM®. The outlet from Chamber B was then connected by TYGON® tubing to a filter holder containing a Cambridge filter (44 mm diameter) used to collect the reaction product. See Pillsbury H C, Smoking machine parameters for collection of total particulate matter and gases from low ignition-potential cigarettes. Under contract to the U.S. Consumer Product Safety Commission #CPSC-S-92-5472 Ii Mar. 14, 1993. The opposing side of the filter housing was connected to a 100 cc syringe by TYGON® tubing. The syringe was affixed to an automated system making up the Controlled Puff Volume Apparatus (CPVA). For detailed methodology, See Levin E D, Rose J E and Behm F. Controlling puff volume without disrupting smoking topography. *Behavior Research Methods Instruments & Computers*, 21:383-386, 1989, the teachings of which are incorporated by reference herein. The total time to prepare the set-up from filling the first chamber to initiating the first sampling interval was approximately 5 minutes. The CPVA was programmed to pull a volume of 35 cc air at 2 seconds duration (30 second intervals) for 20 times (20 puffs). The filled chambers were immersed at half height into a water bath and were allowed to equilibrate at 70° C. for 10 minutes prior to sampling.

Prior to the evaluation of the candidate acids, a control experiment was conducted in which only the nicotine free base was kept in a chamber and nicotine vapors were pulled through a Cambridge filter for 20 times (20 puffs of 35 cc air in 2 seconds duration and 30 seconds puff interval). All the samples were quantified by Gas Chromatography (GC) utilizing a NPD (nitrogen phosphorous detector).

Results:

The following table shows the results of the acid screen as well as the control experiment. Results are reported by the amount of nicotine measured in each puff.

TABLE 2

Nicotine Delivery of Acid Over Base at ~70° c.

| Sample ID | Nicotine (µg)/puff |
|---|---|
| Nicotine Control | 46.12 |
| 4-Methyl-2-oxovaleric acid over Nicotine | 281.39 |
| Isovaleric acid over Nicotine | 25.00 |
| Caprylic acid (Octanoic acid) over Nicotine | 29.44 |
| 2-Oxooctanoic acid over Nicotine | 90.48 |
| Glycolic acid over Nicotine | 35.32 |
| Caproic acid over Nicotine | 14.97 |
| Levulinic acid over Nicotine | 39.93 |
| 2-Oxovaleric acid over Nicotine | 297.75 |
| Propionic acid over Nicotine | 09.68 |
| Pyroligneous acid over Nicotine | 32.54 |
| 2-Mercaptopropionic acid over Nicotine | 19.29 |
| 4-Pentenoic acid over Nicotine | 24.92 |
| 2-Nonenoic acid over Nicotine | 39.84 |
| Geranic acid over Nicotine | 40.54 |
| 3-Methyl-2-oxovaleric acid over Nicotine | 363.89 |
| 2-Methyl-4-pentenoic acid over Nicotine | 26.03 |
| 3-Cyclohexane-1-carboxylic acid over Nicotine | 48.24 |
| Glyoxylic acid over Nicotine | 35.17 |
| Lactic acid over Nicotine | 39.88 |
| Oleic acid over Nicotine | 48.45 |
| Trimethylpyruvic acid over Nicotine | 26.69 |
| Pyruvic acid over Nicotine | 362.28 |
| 3-Methyl-2-oxobutanoic acid over Nicotine | 213.99 |

Discussion:

The experimental results show that at approximately 70° C., 3-Methyl-2-oxovaleric acid over nicotine delivers the greatest amount of nicotine (363.89 µg/puff), followed by Pyruvic acid (362.28 µg/puff), 2-Oxovaleric acid (297.75 µg/puff), 4-Methyl-2-oxovaleric acid (281.39 µg/puff), 3-Methyl-2-oxobutanoic acid (213.99 µg/puff) and 2-Oxooctanoic acid 90.48 μg/puff. These candidates were evaluated under ambient conditions as described in the following experiment. 3-Methyl-2-oxovaleric acid, Pyruvic acid, 2-Oxovaleric acid, 4-Methyl-2-oxovaleric acid, 3-Methyl-2-oxobutanoic acid and 2-Oxooctanoic acid represent the genus of carboxylic acids termed "2-Keto acids" or "Alpha-Keto acids."

Experiment #3: Evaluation of Leading Acid Candidates Under Ambient Temperature Objective:

The objective of this experiment was to assess which of the leading acid candidates selected from the experiment described above will deliver the greatest amount of nicotine under ambient conditions.

Experimental Design:

The current experiment was carried out as described in the previous experiment except that the glass chambers were not immersed in a heated water bath, but sampled at ambient temperature. Individual experiments were carried out using the selected acid candidates: 3-Methyl-2-oxovaleric acid, Pyruvic acid, 2-Oxovaleric acid, 4-Methyl-2-oxovaleric acid, 3-Methyl-2-oxobutanoic acid and 2-Oxooctanoic acid. For each experiment a different acid was placed in Chamber A as in the previous experiment with nicotine free base in Chamber B. A nicotine free base control experiment was also conducted as in the previous experiment.

Results:

The following table shows the results of the assessment of the leading acid candidates sampled under ambient conditions. Results are reported as the amount of nicotine measured in each puff.

TABLE 3

Nicotine Delivery Using Selected Acids Over Base (Ambient Temperature)

| Sample ID | Nicotine (μg)/puff |
|---|---|
| Nicotine base control | 08.76 |
| 3-Methyl-2-oxovaleric acid over nicotine | 12.93 |
| Pyruvic acid over nicotine | 44.68 |
| 2-Oxovaleric acid over nicotine | 18.96 |
| 4-Methyl-2-oxovaleric acid over nicotine | 13.63 |
| 2-Oxooctanoic acid over nicotine | 04.46 |
| 3-Methyl-2-oxobutanoic acid over nicotine | 18.65 |

Discussion:

The data from ambient temperature shows that the Pyruvic acid is the superior candidate to form nicotine aerosol with the delivery of 44.68 μg/puff.

Experiment #4: Assessment of Leading Acid Candidates from the Previous 70° C. and Ambient Temperature Experiments (Experiment 2 and 3 Respectively) Utilizing the Prior Art Design for Aerosol Generation Objective:

The objective of this experiment was to compare the prior art configuration to the sequential orientation of acid and base to determine which yields higher nicotine delivery. The two leading acid candidates which generated similar nicotine delivery at ~70° C. and one acid candidate which delivered the highest amount of nicotine under ambient temperature (from Experiments #2-3) were tested under 70° C. and ambient conditions, respectively.

Experimental Design:

In this experiment, two identical rectangular glass chambers exactly like those used in Experiment #2 were employed. Chamber A contained 2000, of the leading acid and chamber B contained 200 μL of nicotine free base. The two chambers were connected via a "Y" shaped glass connector which was then connected to the same PTFE housing containing a Cambridge filter as described previously. The vapors from the tubes were allowed to be admixed instantly in the "Y" shaped glass connector upon pulling a volume of 35 cc air in 2 seconds duration (30 seconds interval) for 20 times (20 puffs) using a controlled puff volume apparatus (CPVA). For the elevated temperature experiments, the acid and nicotine chambers were immersed at half height into a water bath with a water temperature of approximately 70° C. The chambers were allowed to equilibrate for 10 minutes prior to sampling. For the ambient room temperature experiments, both the chambers were placed on a laboratory bench. The collected samples were analyzed for nicotine using gas chromatography with a nitrogen phosphorous detector.

Results:

The following table shows the results of the assessment of the leading acid candidates sampled at an elevated temperature (approximately at 70° C.) and ambient conditions and employing prior art systems; also reported for comparison are the results using a sequential acid-over-base design (from Experiments #2-3). Results are reported as the mass of nicotine measured in each puff.

TABLE 4

Nicotine Delivery Using a "Y" Shaped Design (Prior Art)

| Sample ID | Nicotine (μg)/puff Prior Art (Y-Connector) | Nicotine (μg)/puff Sequential Design |
|---|---|---|
| At ~70° C. | | |
| 3-Methyl-2-oxovaleric acid and nicotine | 11.50 | 363.89 |
| Pyruvic acid and nicotine | 23.00 | 362.28 |
| At ambient room temperature | | |
| Pyruvic acid and nicotine | 3.26 | 144.68 |

Discussion:

Based on the current data the nicotine delivery in the prior art design is significantly lower than the sequential design and hence the sequential design is the superior method for the delivery of nicotine aerosol.

Experiment #5: Effectiveness of a Sequential Arrangement of an Acid Reservoir and a Base Reservoir to Provide an Acid Over Base Environment in the Development of an Aerosol Plume with Sufficient Concentrations of Nicotine Objective:

The objective of this experiment was to determine the influence of the arrangement of the acid and base reservoirs in sequence allowing the acid vapors to be lifted into the nicotine free base chamber and over the nicotine to generate a plume cloud with sufficient quantities of nicotine free base. Pyruvic acid was selected for use in this experiment.

Experimental Design:

The experimental design was the same as in Experiment #2. This experiment was divided into two parts, A and B. The first part, A, involved the assessment of the use of 200 μL each of nicotine free base and pyruvic acid in separate chambers collected over 3 samples (20 puffs per sample). The second part of the experiment (part B) involved a comparison of the above system tested under ambient and 40° C. conditions to evaluate the effect of mild heat on aerosol formation and nicotine delivery.

Results (Part A):

The following tables show the results of the pyruvic acid over nicotine free base experiment under ambient conditions (part A). Results are reported by the total mass of nicotine and the amount of nicotine measured in each puff.

TABLE 5

Nicotine Delivery of Acid Over Base

| Sample ID | Total Nicotine (μg)/sample | Nicotine (μg)/puff |
|---|---|---|
| Pyruvic acid over Nicotine free base-1 | 782.16 | 39.11 |
| Pyruvic acid over Nicotine free base-2 | 623.02 | 31.15 |
| Pyruvic acid over Nicotine free base-3 | 533.73 | 26.69 |
| | Mean (Coefficient of Variation (CV)) | 32.31 (19.5%) |

Discussion (Part A):

These results indicate that there is an overall decline in nicotine yield from the first sample to the last, by about 32%.

Results (Part B)

The following tables show the results of the pyruvic acid over nicotine free base experiment at 40° C. Results are reported by the total mass of nicotine and the amount of nicotine measured in each puff.

TABLE 6

Nicotine Delivery of Acid Over Base at 40° C.

| Sample ID | Total Nicotine (μg)/sample | Nicotine (μg)/puff |
|---|---|---|
| Pyruvic acid over Nicotine free base-1 | 2341.09 | 117.05 |
| Pyruvic acid over Nicotine free base-2 | 2141.20 | 107.06 |
| Pyruvic acid over Nicotine free base-3 | 2137.92 | 106.90 |
| | Mean (CV) | 110.337 (5.3%) |

Discussion (Part B):

A 3 to 4 fold increase in the mass of Nicotine/puff was observed under heated conditions when compared to ambient conditions. Further, the coefficient of variation significantly improved to about 5% representing good control of the delivery dynamics. Moreover, there was no significant decline in nicotine delivery across puffs.

Experiment #6: Investigation of Nicotine Aerosol Formation and Delivery by Using the Sequential Set Up with Pyruvic Acid in a Miniaturized/Cigarette Sized Device (8 cm long and 8 mm ID)

Materials and Method

Matrix Materials Used:

Air-freshener wick samples made of a blend of PE and PP fibers (sold as X-40495 fiber from Porex Technologies) were used as a matrix upon which pyruvic acid was loaded and GORE™ Medical Membrane (pore size of 0.2 micron) consisting of an expanded PTFE medical membrane with a non-woven PET membrane support (sold as SMPL-MMT314 from W.L. Gore & Associates, Inc.) was used as a matrix to load nicotine free base. The membrane sheet was rolled into a straw configuration to provide a polyester inner wall and TEFLON® outer wall having approximate dimensions of 1.5 mm ID and cut into 4 cm long pieces.

Experimental Design:

A piece of air-freshener wick was loaded with 180 μL of pyruvic acid (pyruvic acid source element) and the inner walls (polyester side) of three pieces of the 4 cm long and 1.5 mm ID rolled medical membrane were coated with 90 μL (3×30 μL) of nicotine free base. The air freshener with loaded pyruvic acid was inserted into the distal end of 8 mm ID and 9 cm long clear TEFLON® tube and the three pieces of the medical membrane with nicotine free base were inserted tightly into a TEFLON® washer which had three holes (nicotine source element). The nicotine source element was inserted into the 9 cm long, 8 mm internal diameter (ID) TEFLON® tube with the pyruvic acid source element leaving a gap between the pyruvic acid source element and nicotine source element of 2 cm. The arrangement of the source elements were in such a way that a measured volume of air (35 cc at 2 sec duration and 30 second puff interval for 20 times) pulled by automated syringe pump traveled first through the pyruvic acid source element and then through the nicotine source element to form an aerosol. The proximal end of the device was connected to a controlled puff volume apparatus (CPVA) containing a Cambridge filter (to collect aerosol product). For the elevated temperature (40° C.) experiment, the 9 cm long device (which had both pyruvic acid and nicotine source elements) was completely immersed in a water bath and equilibrated for 10 minutes prior to sampling. The ambient condition experiment was carried out by placing the chambers on a laboratory bench.

Results:

The samples were analyzed for nicotine content and reported in Table 7 and Table 8.

TABLE 7

Nicotine Delivery in a Miniaturized Device Experiment at ~40°

| Sample ID | Nicotine (μg)/puff |
|---|---|
| Pyruvic acid in air-freshener wick over nicotine in three rolled pieces of medical membrane | 103.58 |

TABLE 8

Nicotine Delivery in a Miniaturized Device Experiment at Ambient Temperature

| Sample ID | Nicotine (μg/puff) |
|---|---|
| Pyruvic acid in air-freshener wick over nicotine in three rolled pieces of medical membrane | 29.20 |

Discussion:

The data indicates that when both the acid and base were loaded onto a matrix, in this case, air-freshener wick for acid and medical membrane for nicotine free base, a comparable nicotine delivery was obtained as with the previous experimental apparatus used in Experiment 5. In addition, the ~40° C. condition showed significantly higher amount of nicotine delivery (approximately threefold) when compared to the ambient condition.

Improvement Experiments

Experiment #1: Screening for Suitable Chemical Agents for Nicotine to Improve the Efficiency of Aerosol Formation with Pyruvic Acid Objective:

The current experiment was conducted to identify a suitable chemical agent for nicotine to form an efficient aerosol with pyruvic acid vapor.

Materials and Method:

Nicotine Bitartrate Solutions:

Nicotine base was prepared as per the following procedures:

About 16 mg of nicotine bitartrate (equivalent to 5 mg of nicotine base) was mixed with 200 mg of sodium hydroxide pellets in a side arm test tube and 1 mL of distilled water was added and vortexed [NaOH Nicotine base].

About 16 mg of nicotine bitartrate (equivalent to 5 mg of nicotine base) was mixed with 200 mg of calcium hydroxide in a side arm test tube and 1 mL of distilled water was added and vortexed [$Ca(OH)_2$ Nicotine base].

About 16 mg of nicotine bitartrate (equivalent to 5 mg of nicotine base) was mixed with 200 mg of potassium hydroxide in a side arm test tube and 1 mL of distilled water was added and vortexed [KOH Nicotine base].

About 16 mg of nicotine bitartrate (equivalent to 5 mg of nicotine base) in a side arm test tube was dissolved in 1 mL of distilled water and heated to 75-80° C. (temperature to match with exothermic condition) [Control for exothermic experiment]

About 16 mg of nicotine bitartrate (equivalent to 5 mg of nicotine base) in a side arm test tube was dissolved in 1 mL of distilled water [Control for ambient temperature experiment]

Pyruvic Acid:

About 1 mL of pyruvic acid was measured into a side arm glass test tube for each experiment and the air flow was introduced through a Pasteur pipette.

Testing Procedure:

Two identical side arm glass tubes (Tube A and B) were used for this experiment. Tube A contained about 1 ml pyruvic acid and Tube B contained alkalinized nicotine. The nicotine with bases or nicotine alone (control) in an independent side arm test tube was immediately connected to the pyruvic acid source (measuring temperature as an index of the exothermic process resulting from the addition of water to the selected base). For the ambient temperature condition experiments, the nicotine tube was cooled down to room temperature prior to connecting to pyruvic acid tube. The pyruvic acid vapor (from Tube A) was passed over the nicotine mixed with chemical agent (Tube. B) and the outlet from tube B was connected to a Cambridge filter to collect the reaction product upon pulling a volume of 35 cc air at 2 seconds duration (5 seconds interval) for 5 times (5 puffs), 10 times (10 puffs), 20 times (20 puffs) or 50 times (50 puffs) by using an automated syringe pump. The vapor formed in Tube A was introduced into Tube B by means of air flowing through a glass pipette attached to Tube A. All the samples were quantified by Gas Chromatography (GC) utilizing a NPD (nitrogen phosphorous detector).

Results:

The samples were analyzed for nicotine content and the mean amount of nicotine delivered in aerosol form is furnished in Table 1A and 1B.

TABLE 1A

Nicotine delivery when pyruvic acid vapor passed over mixture of nicotine bitartrate and base solutions under exothermic heat condition

| | Nicotine (μg/puff) delivered in aerosol when pyruvic acid passed over: | | | |
|---|---|---|---|---|
| Sample ID | NaOH & Nicotine (mean of 20 puffs) Under exothermic heat condition | $Ca(OH)_2$ & Nicotine (mean of 20 puffs) Under exothermic heat condition | KOH & Nicotine (mean of 20 puffs) Under exothermic heat condition | Control Nicotine (mean of 20 puffs) (Heated to 75-80° C.) |
| 1 | 40.6 | 1.2 | 38.7 | 0.9 |
| 2 | 32.6 | 0.5 | 36.1 | 1.6 |
| 3 | 30.8 | 0.7 | 30.2 | 1.2 |
| 4 | 26.3 | 0.4 | 24.5 | 1.6 |
| 5 | 26.3 | 0.4 | 19.5 | 1.0 |
| Mean Nicotine (100 puffs) μg ± SD | 31.33 ± 5.86 | 0.66 ± 0.35 | 29.79 ± 7.94 | 1.25 ± 0.35 |

TABLE 1B

Nicotine delivery when pyruvic acid vapor passed over mixture of nicotine bitartrate and base solutions at ambient temperature

| | Nicotine (μg/puff) delivered in aerosol when pyruvic acid passed over: | | | |
|---|---|---|---|---|
| Sample ID | NaOH & Nicotine (mean of 20 puffs) At room temperature | $Ca(OH)_2$ & Nicotine (mean of 20 puffs) At room temperature | KOH & Nicotine (mean of 20 puffs) At room temperature | Control Nicotine (mean of 20 puffs At room temperature |
| 1 | 35.2 | 0.8 | 34.2 | 1.1 |
| 2 | 32.8 | 0.5 | 35.1 | 1.2 |
| 3 | 22.8 | 0.3 | 29.9 | 0.2 |
| 4 | 22.3 | 0.3 | 25.8 | 0.2 |
| 5 | 23.2 | 0.3 | 22.8 | 0.1 |
| | Mean Nicotine (100 puffs) μg ± SD = 27.26 ± 6.21 | Mean Nicotine (100 puffs) μg ± SD = 0.43 ± 0.23 | Mean Nicotine (100 puffs) μg ± SD = 29.57 ± 5.29 | Mean Nicotine (100 puffs) μg ± SD = 0.55 ± 0.55 |

Discussion:

The nicotine aerosol delivery obtained from the experiments that were conducted by mixing three different bases [NaOH, KOH and $Ca(OH)_2$] with nicotine base demonstrated a distinguishable outcome. In addition, the two experimental conditions (under exothermic heat condition and ambient temperature condition) have also produced different results with respect to the nicotine aerosol delivery.

Under the exothermic heat condition, the mean nicotine aerosol deliveries were 31.33 μg/puff when nicotine base mixed with sodium hydroxide (NaOH), 0.66 μg/puff when nicotine base mixed with calcium hydroxide [$Ca(OH)_2$] and 29.79 μg/puff when nicotine base mixed with potassium hydroxide (KOH). The control experiment has delivered about 1.25 μg/puff of nicotine aerosol under the identical experimental condition without any chemical agent (base). It is important to note that the mixing of [$Ca(OH)_2$] with water and nicotine base did not generate any heat while other two bases (NaOH and KOH) did generate heat. The sodium hydroxide and potassium hydroxide are known as "alkali metal hydroxides" while the calcium hydroxide as "alkaline earth metal hydroxide". The current experimental results indicate that the nicotine aerosol delivery was significantly enhanced when the nicotine base mixed with alkali metal hydroxides when compared to alkaline earth metal hydroxide under identical test conditions.

When the experiments were conducted at ambient (room) temperature, the mean nicotine aerosol deliveries were 27.26 μg/puff when nicotine base was mixed with sodium hydroxide (NaOH), 0.43 μg/puff when nicotine base was mixed with calcium hydroxide [$Ca(OH)_2$] and 29.57 μg/puff when nicotine base was mixed with potassium hydroxide (KOH). The control experiment delivered about 0.55 μg/puff of nicotine aerosol under the identical experimental condition without any base. Interestingly, at room temperature the nicotine aerosol delivery was slightly higher when the nicotine base was mixed with KOH when compared to the NaOH.

The nicotine delivery in the experiment that used potassium hydroxide (an alkali metal hydroxide) was slightly increased relative to NaOH. Hence, the following experiments were conducted using potassium hydroxide as a preferred agent.

Experiment #2: Pyruvic Acid Passed Over Nicotine Bitartrate and Potassium Hydroxide Mixture Under Exothermic Heat Objective:

In the earlier experiments, it was noted that the heat released from the exothermic reaction played a significant role in enhancing the initial nicotine delivery in aerosol form. The current investigation was carried out to test the sustainability of the enhancement of nicotine aerosol delivery by exothermic heat. Nicotine bitartrate was used as a source of nicotine base for this experiment.

Materials and Method:

Alkalinized Nicotine Bitartrate Solutions:

Two different concentrations of alkalinized nicotine base were prepared using the following procedures:

About 250 mg of nicotine bitartrate salt (equivalent to 81 mg of nicotine base) was mixed with 500 mg of potassium hydroxide pellets in a side arm test tube and 1 mL of distilled water was added and mixed thoroughly.

About 125 mg of nicotine bitartrate salt (equivalent to 40 mg of nicotine base) was mixed with 250 mg of potassium hydroxide pellets in a side arm test tube and 1 mL of distilled water was added and mixed thoroughly.

Pyruvic Acid:

About 1 mL of pyruvic acid was measured into a side arm glass test tube for each experiment and the air flow was introduced through a Pasteur pipette.

Testing Procedure:

The alkalinized nicotine base solution in an independent side arm test tube was connected to the pyruvic acid source as per the method described in Experiment #1.

Results:

The samples were analyzed for nicotine content and the mean amount of nicotine delivered in each 50 puffs for up to 150 puffs are furnished in Table 2.

TABLE 2

Nicotine delivery when pyruvic acid vapor passed over alkalinized nicotine bitartrate solutions under exothermic heat condition

| | Nicotine (μg/puff) delivered in aerosol when: | |
|---|---|---|
| Sample ID | Pyruvic acid passed over 81 mg alkalinized nicotine base (Experiment-A) | Pyruvic acid passed over 40 mg alkalinized nicotine base (Experiment-B) |
| 50 puffs-1 | 76.7 | 57.8 |
| 50 puffs-2 | 32.4 | 24.1 |
| 50 puffs-3 | 24.5 | 19.2 |

Discussion:

The results showing the amount of nicotine delivered in the first 50 puffs (76.7 µg/puff in Experiment-A and 57.8 µg/puff in Experiment-B) suggest that the heat generated from the exothermic reaction, as a result of reaction between potassium hydroxide and water, dramatically enhanced the nicotine aerosol formation with pyruvic acid in the first 50 puffs; the time required to complete 50 puffs was about 30 minutes, during which the heat generated from the exothermic reaction sustained an elevated temperature. The current experimental results are significant and unique in the sense that there was no external heating required to obtain the enhanced nicotine delivery in the first 50 puffs. This result again confirms our prior application's use of heat to enhance delivery of nicotine and demonstrates that this alternative mechanism for heating can be applied to enhance deliver for a number of puffs representing a practical and commercially viable option. With proper insulation, the exothermic heat should be useful for enhancing delivery through even more that the 50 puffs shown here.

Experiment #3: Pyruvic Acid Passed Over Nicotine Bitartrate and Potassium Hydroxide Mixture Objective:

The current experiment was designed to investigate the nicotine delivery in aerosol form when the pyruvic acid vapor was passed over the alkalinized nicotine base. Nicotine bitartrate was used as the source of nicotine base.

Materials and Method:

Alkalinized Nicotine Bitartrate Solution:

About 500 mg of nicotine bitartrate salt (equivalent to 162 mg of nicotine base) was mixed with 1 g of potassium hydroxide pellets in a side arm test tube and 2 mL of distilled water was added and mixed thoroughly.

Pyruvic Acid:

About 1 mL of pyruvic acid was measured into a side arm glass test tube for each experiment and the air flow was introduced through a Pasteur pipette.

Testing Procedure:

The alkalinized nicotine base solution in independent side arm test tubes was immediately (so exothermic heat could be measured) connected to the pyruvic acid source as per the method described in Experiment #1.

Results:

The samples were analyzed for nicotine content and the mean amounts of nicotine delivered in each 50 puffs of 35 cc volume are furnished in Table 3. The results were compared with the data obtained from an identical experimental design with a relatively equivalent amount (700 µL) of pyruvic acid and significantly higher amount (700 mg) of non-alkalinized nicotine base.

TABLE 3

Nicotine delivery when pyruvic acid vapor passed over alkalinized nicotine bitartrate solution at room temperature compared to nicotine delivery from non-alkalinized nicotine base

| | Nicotine (µg/puff) delivered in aerosol | |
|---|---|---|
| Sample ID | Pyruvic acid over 162 mg alkalinized nicotine bitartrate (each point is mean of 50 puffs) | Pyruvic acid over 700 mg non-alkalinized nicotine base (each point is mean of 40 puffs) |
| 1 | 91.9 | 27.93 |
| 2 | 74.9 | 25.30 |
| 3 | 63.2 | 22.41 |
| 4 | 54.5 | 17.38 |
| 5 | N/A | 15.30 |
| Mean nicotine (in 200 puffs) ± SD | 71.12 ± 16.15 | 21.66 ± 5.29 |

Discussion:

It was remarkable that the nicotine delivery in the 200 puffs (mean of 71.12 µg/puff) of the current experiment was dramatically increased (about 3.5 folds) when compared to the previous experimental results (the mean nicotine value was 21.66 µg/puff). More importantly, the amount of total nicotine free base used in the current experiment was significantly lower (162 mg) than the previous experiment (700 mg). Another important finding was that the nicotine delivered in the first 50 puffs was higher than the subsequent puffs. We observed that when the nicotine salt reacted with potassium hydroxide and water, there was a significant amount of energy released in the form of heat (exothermic heat). The elevated temperature (about 80° C.) was sustained for about 15 to 20 minutes. Therefore, the increased nicotine delivery in the first 50 puffs was probably due to the exothermic heat. Importantly, however, the enhanced delivery of nicotine in puffs 100-200 cannot readily be attributed to a transient exothermic response. Rather, the addition of alkali metal hydroxides with the nicotine per se (that is some effect of the addition of base beyond exothermic heating) appears to be responsible for the sustained increase in the yield of nicotine aerosol. From the current experimental data, it can be concluded that the use of an agent from alkali metal hydroxides has helped reduce the amount of nicotine base needed to form an efficient aerosol with significantly enhanced nicotine aerosol delivery when compared to the control experiment (in which there was no alkali metal hydroxide present).

These observations led us to conduct the next set of experiments using small quantities of nicotine salts.

Experiment #4: Pyruvic Acid Passed Over Reduced Amount of Nicotine Bitartrate in Potassium Hydroxide Mixture at Room Temperature Objective:

The current experiment was designed to determine the smallest amount of nicotine bitartrate that can be used to form an efficient aerosol with pyruvic acid vapor. For this purpose, three different amounts of nicotine bitartrate were used as a source of nicotine base to form an aerosol with pyruvic acid vapor. The aerosol samples were collected in the absence of exothermic heat by waiting for the tubes to reach room temperature.

Materials and Method:

Nicotine Bitartrate Solutions:

The three different concentrations of alkalinized nicotine base for the current experiments were prepared as follows:

About 32 mg of nicotine bitartrate salt (equivalent to 10 mg of nicotine base) was mixed with 100 mg of potassium hydroxide pellets in a side arm test tube and 200 µL of distilled water was added and mixed thoroughly.

About 20 mg of nicotine bitartrate salt (equivalent to 6.5 mg of nicotine base) was mixed with 100 mg of potassium hydroxide pellets in a side arm test tube and 200 µL of distilled water was added and mixed thoroughly.

About 9 mg of nicotine bitartrate salt (equivalent to 2.9 mg of nicotine base) was mixed with 100 mg of potassium hydroxide pellets in a side arm test tube and 200 µL of distilled water was added and mixed thoroughly.

The above solutions in independent side arm test tubes were kept at room temperature for 20 minutes to allow the tubes to reach room temperature.

Pyruvic Acid:

About 1 mL of pyruvic acid was measured into a side arm glass test tube for each experiment and the air flow was introduced through a Pasteur pipette.

Testing Procedure:

The method described in Experiment #1 was followed here.

Results:

The samples were analyzed for nicotine content and the mean amount of nicotine delivered in each 10 puffs for the first 100 puffs are furnished in Table 4.

TABLE 4

Nicotine delivery when pyruvic acid vapor passed over mixture of lower concentrations of nicotine and potassium hydroxide solution at room temperature

| Sample ID | Nicotine (µg/puff) delivered in aerosol form (µg)/puff when | | |
|---|---|---|---|
| | Pyruvic acid over 10 mg of nicotine in potassium hydroxide | Pyruvic acid over 6.5 mg nicotine in potassium hydroxide | Pyruvic acid over 2.9 mg nicotine in potassium hydroxide |
| 10 puffs-1 | 50.5 | 46.6 | 46.2 |
| 10 puffs-2 | 53.5 | 35.3 | 33.6 |
| 10 puffs-3 | 49.5 | 36.7 | 27.5 |
| 10 puffs-4 | 35.9 | 24.2 | 26.0 |
| 10 puffs-5 | 33.8 | 23.4 | 21.7 |
| 10 puffs-6 | 31.2 | 24.4 | 21.9 |
| 10 puffs-7 | 28.3 | 23.8 | 19.5 |
| 10 puffs-8 | 25.7 | 23.3 | 17.9 |
| 10 puffs-9 | 24.1 | 22.3 | 17.9 |
| 10 puffs-10 | 22.9 | 20.7 | 18.8 |
| Mean nicotine (in 100 puffs) ± SD | 35.55 ± 11.57 | 28.07 ± 8.48 | 25.10 ± 8.94 |

Discussion:

The experimental results demonstrate that the mean amount of nicotine delivered in the first 100 puffs of aerosol was 35.55 µg/puff with a small amount (10 mg) of nicotine in potassium hydroxide solution, 28.07 µg/puff with a smaller amount (6.5 mg) of nicotine in potassium hydroxide solution, and 25.10 µg/puff with the smallest amount (2.9 mg) of nicotine in potassium hydroxide solution. All three experiments have exhibited significant nicotine aerosol delivery even at significantly lower level of nicotine when compared to the earlier experiment in which about 700 mg of nicotine base was used (Table 3). Incidentally, the nicotine aerosol delivery with the smallest amount (2.9 mg) of alkalinized nicotine was superior to the experiment that used 700 mg of nicotine base. It was remarkable to note that the addition of potassium hydroxide to the nicotine bitartrate solution forms such an efficient nicotine aerosol even using small amounts of nicotine.

It can be concluded that the combining nicotine bitartrate with potassium hydroxide was helpful in overcoming the fall off in nicotine aerosol delivery for the first 100 puffs even at significantly lower concentrations of nicotine base.

Experiment #5: Evaluation of Mass Balance for Nicotine Delivered in Aerosol when Pyruvic Acid is Passed Over a Nicotine Bitartrate and Potassium Hydroxide Mixture Objective:

The primary objective of the current experiment was to investigate the amount of nicotine delivered in aerosol form and to calculate the percentage of recovery for nicotine. The secondary aim was to determine the sustainability of a desirable amount of nicotine delivery in two different concentrations of nicotine bitartrate and potassium hydroxide solutions.

Materials and Method:

Nicotine Bitartrate Solutions:

Two different concentrations of nicotine base were prepared as per the following procedures:

About 32 mg of nicotine bitartrate salt (equivalent to 10 mg of nicotine base) was mixed with 100 mg of potassium hydroxide pellets in a side arm test tube and 200 µL of distilled water was added and mixed thoroughly.

About 9 mg of nicotine bitartrate salt (equivalent to 2.9 mg of nicotine base) was mixed with 100 mg of potassium hydroxide pellets in a side arm test tube and 200 µL of distilled water was added and mixed thoroughly.

The above solutions in independent side arm test tubes were kept at room temperature for 20 minutes to prevent any influence of exothermic heat on the nicotine aerosol formation.

Pyruvic Acid:

About 1 mL of pyruvic acid was measured into a side arm glass test tube for each experiment and the air flow was introduced through a Pasteur pipette.

Testing Procedure:

The alkalinized nicotine base solutions in an independent side arm test tube were connected to the pyruvic acid source as per the method described in Experiment #1.

Results:

The samples were analyzed for nicotine content and the mean amount of nicotine delivered in each 10 puffs is furnished in Table 5:

TABLE 5

Nicotine delivery when pyruvic acid vapor passed over the mixture of nicotine bitartrate and potassium hydroxide solutions

| | Nicotine (µg/puff) delivered in aerosol using: | |
|---|---|---|
| Sample ID (10 puffs/sample) | Pyruvic acid over 10 mg alkalinized nicotine base | Pyruvic acid over 2.9 mg alkalinized nicotine base |
| 1 | 45.5 | 44.9 |
| 2 | 45.0 | 37.5 |
| 3 | 44.4 | 27.7 |
| 4 | 42.4 | 20.9 |
| 5 | 41.5 | 23.0 |
| 6 | 36.9 | 24.2 |
| 7 | 37.4 | 22.1 |
| 8 | 40.3 | 25.6 |
| 9 | 36.8 | 20.0 |
| 10 | 33.2 | 17.6 |
| 11 | 33.1 | 13.9 |
| 12 | 29.3 | 11.0 |
| 13 | 32.2 | 0.0 |
| 14 | 32.0 | 0.0 |
| 15 | 30.9 | 0.0 |

TABLE 5-continued

Nicotine delivery when pyruvic acid vapor passed over the mixture of nicotine bitartrate and potassium hydroxide solutions

| | Nicotine (μg/puff) delivered in aerosol using: | |
|---|---|---|
| Sample ID (10 puffs/sample) | Pyruvic acid over 10 mg alkalinized nicotine base | Pyruvic acid over 2.9 mg alkalinized nicotine base |
| 16 | 27.5 | N/A |
| 17 | 31.2 | N/A |
| 18 | 23.8 | N/A |
| 19 | 25.5 | N/A |
| 20 | 27.1 | N/A |
| 21 | 22.7 | N/A |
| 22 | 22.6 | N/A |
| 23 | 20.6 | N/A |
| 24 | 20.6 | N/A |
| 25 | 23.0 | N/A |
| 26 | 24.4 | N/A |
| 27 | 20.7 | N/A |
| 28 | 20.9 | N/A |
| | Mean Nicotine (in 280 puffs) μg ± SD = 31.13 ± 8.21 Total amount of nicotine delivered in 280 puffs = 7.9 mg Recovery = 79.0% | Mean Nicotine (in 120 puffs) μg ± SD = 24.03 ± 9.43 Total amount of nicotine delivered in 120 puffs = 2.88 mg Recovery = 99.3% |

Discussion:

The total amount of nicotine delivered in the first 280 puffs from the experiment that contained 10 mg of nicotine in potassium hydroxide was about 7.9 mg with a mean nicotine amount of 31.13 μg/puff. The sum of nicotine delivered (in 120 puffs) in the experiment that contained about 2.9 mg of alkalinized nicotine base was 2.88 mg with a mean nicotine amount of 24.03 μg/puff. The aerosol formation and delivery was still present (as evidenced from the double digits nicotine delivery observed at $280^{th}$ puff) in the experiment that contained about 10 mg alkalinized nicotine base; while the aerosol formation lasted only 120 puffs in the experiment in which about 2.9 mg alkalinized nicotine base was used. It was remarkable to note that the recovery was about 99.3% in the experiment where 2.88 mg of alkalinized nicotine base used and 79.0% recovery where 10 mg alkalinized nicotine base was used. Therefore, the current experimental results have clearly demonstrated that most of the nicotine (more than 79%) has been efficiently utilized to form an aerosol with pyruvic acid. Furthermore, the current experimental results showed that the sustainability of nicotine aerosol delivery depends upon the amount of nicotine in potassium hydroxide used.

Experiment #6: Investigations to Develop a Suitable Device to Generate and Deliver Nicotine Pyruvate Aerosol Objective:

The aim of the current set of experiments was to move the laboratory design toward making a commercially usable device.

Design #1: Pyruvic Acid in Side Arm Test Tube and Nicotine Base in 2 mm ID Glass Tubes
Materials and Methods
Nicotine Base Solution:

About 10 μL (10 mg) of nicotine base was mixed with 30 μL of saturated solution of potassium hydroxide. The solution was coated (4×10 μL) onto the inner surfaces of 4 pieces of 10 cm long and 2 mm ID glass tubes and the coated tubes were housed in an 8 mm ID Teflon tube (Nicotine base unit).

Pyruvic Acid:

About 1 mL of pyruvic acid (PA) was measured into a side arm glass test tube for each experiment and the air flow was introduced through a Pasteur pipette (Pyruvic acid unit).

Testing Procedure:

The nicotine base unit was connected to the pyruvic acid unit and the aerosol samples were collected as per the method described in Experiment #1.

Design #1: Pyruvic Acid in Side Arm Test Tube and Nicotine in Potassium Hydroxide Coated onto Inner Surface of 2 mm ID Glass Tubes
Materials and Methods
Nicotine Base Solutions:

About 10 μL (10 mg) of nicotine base was mixed with 30 μL of saturated solution of potassium hydroxide (KOH). The solution was coated (4×10 μL) onto the inner surfaces of 4 pieces of 10 cm long and 2 mm ID glass tubes and the coated tubes were housed into an 8 mm ID Teflon tube (Nicotine base unit)—Solution 1

About 20 μL (20 mg) of nicotine base was mixed with 20 μL of saturated solution of potassium hydroxide. The solution was coated (4×10 μL) onto the inner surfaces of 4 pieces of 10 cm long and 2 mm ID glass tubes and the coated tubes were housed into an 8 mm ID Teflon tube (Nicotine base unit)—Solution 2

About 30 μL (30 mg) of nicotine base was mixed with 10 μL of saturated solution of potassium hydroxide. The solution was coated (4×10 μL) onto the inner surfaces of 4 pieces of 10 cm long and 2 mm ID glass tubes and the coated tubes were housed into an 8 mm ID Teflon tube (Nicotine base unit)—Solution 3

Pyruvic Acid:

About 1 mL of pyruvic acid (PA) was measured into a side arm glass test tube for each experiment and the air flow was introduced through a Pasteur pipette (Pyruvic acid unit)

Testing Procedure:

The nicotine base unit was connected to the pyruvic acid unit and the aerosol samples were collected as per the method described in Experiment #1 after waiting 20 minutes for the heat from the exothermic reaction to dissipate.

Results:

The samples were analyzed for nicotine content and the mean amounts of nicotine delivered in each 10 puffs of aerosol are furnished in Table 6.

TABLE 6

Nicotine delivery when pyruvic acid in a side arm test tube was passed over alkalinized nicotine base coated onto glass tubes

| | Nicotine (μg/puff) delivered in aerosol using | | |
|---|---|---|---|
| Sample ID | Solution 1* | Solution 2** | Solution 3*** |
| Pyruvic acid over nicotine in KOH-1 | 67.8 | 62.0 | 73.4 |
| Pyruvic acid over nicotine in KOH-2 | 64.5 | 58.6 | 70.0 |
| Pyruvic acid over nicotine in KOH-3 | 56.0 | 57.4 | 68.2 |
| Pyruvic acid over nicotine in KOH-4 | 52.4 | 54.3 | 64.8 |
| Pyruvic acid over nicotine in KOH-5 | 47.6 | 47.6 | 64.2 |
| Pyruvic acid over nicotine in KOH-6 | 43.9 | 48.1 | 67.3 |
| Pyruvic acid over nicotine in KOH-7 | 44.4 | 40.1 | 64.8 |

TABLE 6-continued

Nicotine delivery when pyruvic acid in a side arm test tube was passed over alkalinized nicotine base coated onto glass tubes

| | Nicotine (μg/puff) delivered in aerosol using | | |
|---|---|---|---|
| Sample ID | Solution 1* | Solution 2** | Solution 3*** |
| Pyruvic acid over nicotine in KOH-8 | 44.1 | 35.0 | 64.4 |
| Pyruvic acid over nicotine in KOH-9 | 42.4 | 36.1 | 60.2 |
| Pyruvic acid over nicotine in KOH-10 | 40.7 | 32.2 | 53.8 |
| Mean Nicotine (in 100 puffs) μg ± SD | 50.37 ± 9.5 | 47.14 ± 10.8 | 65.10 ± 5.4 |

*10 μL (10 mg) of nicotine base was mixed with 30 μL of saturated solution of potassium hydroxide;
**20 μL (20 mg) of nicotine base was mixed with 20 μL of saturated solution of potassium hydroxide;
***30 μL (30 mg) of nicotine base was mixed with 10 μL of saturated solution of potassium hydroxide Design #2: Pyruvic Acid and Nicotine in Potassium Hydroxide Coated onto the Inner Surface of 2 mm ID Glass Tube Materials and Methods Nicotine Base Solution:

About 2.7 mg of nicotine base was mixed with 20 μL of saturated solution of potassium hydroxide. The solution was coated onto the inner surface of a 10 cm long and 2 mm ID glass tube and the coated tube was housed in an 8 mm ID Teflon tube (Nicotine base unit).

Pyruvic Acid:

About 20 μL of pyruvic acid (PA) was coated onto the inner surface of a 10 cm long and 2 mm ID glass tube and the coated tube was housed in an 8 mm ID Teflon tube (Pyruvic acid unit).

Testing Procedure:

The nicotine base unit was connected to the pyruvic acid unit and the aerosol samples were collected as per the method described in Experiment #1 after waiting 20 minutes for the heat from the exothermic reaction to dissipate.

Results:

The samples were analyzed for nicotine content and the mean amounts of nicotine delivered in each 5 puffs of aerosol are furnished in Table 7. The results were compared with the data obtained from an identical experiment except that the nicotine base was not mixed with potassium hydroxide solution.

TABLE 7

Nicotine delivery when pyruvic acid coated in glass tube passed over nicotine in potassium hydroxide (KOH) coated in glass tube

| | Nicotine (μg/puff) delivered in aerosol | |
|---|---|---|
| Sample ID | Nicotine in KOH | Nicotine without KOH |
| Pyruvic acid over nicotine-1 | 75.2 | 29.5 |
| Pyruvic acid over nicotine-2 | 53.3 | 30.6 |
| Pyruvic acid over nicotine-3 | 34.9 | 25.1 |
| Mean Nicotine (in 15 puffs) μg ± SD | 54.48 ± 20.14 | 28.36 ± 2.91 |

Design #3: Pyruvic Acid Loaded onto an Air-Freshener Plug and Nicotine Coated onto the Inner Surface of 2 mm ID Glass Tubes Materials and Methods Nicotine Base:

About 5 mg of nicotine base was mixed with 15 μL of saturated solution of potassium hydroxide. The solution was coated onto the inner surface of two 10 cm long and 2 mm ID glass tubes (arranged in parallel) and two more empty glass tubes (uncoated) of the same dimension were included for air dilution. All the tubes were housed in an 8 mm ID Teflon tube (Nicotine base unit).

Pyruvic Acid:

About 140 μL of pyruvic acid (PA) was loaded onto an air-freshener wick sample made of a blend of PE and PP fibers (sold as X-40495 fiber from Porex Technologies) and inserted into a 6 mm ID Teflon tube (Pyruvic acid unit).

Testing Procedure:

The nicotine base unit was connected to the pyruvic acid unit and the aerosol samples were collected as per the method described in Experiment #1 after waiting 20 minutes for the heat from the exothermic reaction to dissipate.

Results:

The samples were analyzed for nicotine content and the mean amount of nicotine delivered in each 10 puffs of aerosol is furnished in Table 8. The results were compared with the data obtained from identical experimental procedures except that the nicotine base was not alkalinized (Non-alkalinized nicotine).

TABLE 8

Nicotine delivery when pyruvic acid was loaded into an air freshener passed over nicotine in potassium hydroxide coated in glass tubes

| | Nicotine (μg/puff) delivered in aerosol | |
|---|---|---|
| Sample ID | Nicotine in KOH | Nicotine without KOH |
| Pyruvic acid over nicotine-1 | 27.5 | 7.1 |
| Pyruvic acid over nicotine-2 | 24.3 | 6.2 |
| Pyruvic acid over nicotine-3 | 24.5 | 6.4 |
| Pyruvic acid over nicotine-4 | 24.6 | 5.7 |
| Pyruvic acid over nicotine-5 | 17.8 | 2.2 |
| Mean Nicotine (in 50 puffs) μg ± SD | 23.7 ± 3.58 | 5.5 ± 1.92 |
| CONTROL EXPERIMENT | | |
| Empty over Nicotine-1 | 3.2 | 3.5 |
| Empty over Nicotine-2 | 3.0 | 3.5 |
| Empty over Nicotine-3 | 3.0 | 2.1 |
| Empty over Nicotine-4 | 2.6 | 2.9 |
| Empty over Nicotine-5 | 2.5 | 2.3 |
| Mean Nicotine (in 50 puffs) μg ± SD | 2.7 ± 0.29 | 2.4 ± 0.65 |

Discussion:

The results of Experiment 6 illustrate the use of device components similar to those that might be employed in practical product designs for delivering a nicotine aerosol for inhalation. A sustained enhancement in nicotine yield, independent of any exothermic reaction, results from the use of an alkali metal hydroxide with nicotine, as in Designs #1-3 described above. In all cases, the substantial delivery of nicotine in the absence of exogenous heating elements demonstrates the utility of employing an alkali metal hydroxide in combination with nicotine to enhance nicotine yield.

Experiment #7: Investigations to Select Appropriate Ratio of Nicotine and Potassium Hydroxide to Generate and Deliver Nicotine Pyruvate Aerosol Objective:

The aim of the current was to select an appropriate ratio of nicotine to potassium hydroxide to generate and deliver sustainable amount of nicotine pyruvate aerosol.

Materials and Methods
Nicotine Base Solution:

About 10 μL (10 mg) of nicotine base was mixed with 200 μL of water which contained 10 or 20 or 40 or 60 or 80 or 100 or 200 mg of potassium hydroxide in a side arm test tube (nicotine base unit). The nicotine base units were kept at room temperature for an hour (to cool down after the generation of exothermic heat) prior to the experiments.

Pyruvic Acid:

About 1 mL of pyruvic acid (PA) was measured into a side arm glass test tube for each experiment and the air flow was introduced through a Pasteur pipette (Pyruvic acid unit).

Testing Procedure:

The nicotine base unit was connected to the pyruvic acid unit and the aerosol samples were collected as per the method described in Experiment #1.

Results:

The samples were analyzed for nicotine content and the mean amount of nicotine delivered in each 20 puffs of aerosol is furnished in Table 10.

TABLE 10

Nicotine delivery when pyruvic acid vapor passed over different ratios of potassium hydroxide and nicotine base Mean Nicotine delivery in 20 puffs (μg/puff) when pyruvic acid vapor passed over nicotine (10 μL), water (200 μL) and

| Sample ID | 10 mg KOH | 20 mg KOH | 40 mg KOH | 60 mg KOH | 80 mg KOH | 100 mg KOH | 200 mg KOH |
|---|---|---|---|---|---|---|---|
| $1^{st}$ 20 puffs | 7.2 | 33.0 | 41.1 | 38.3 | 39.2 | 43.3 | 28.1 |
| $2^{nd}$ 20 puffs | 3.1 | 20.9 | 38.8 | 46.6 | 38.5 | 31.0 | 13.5 |
| $3^{rd}$ 20 puffs | 1.9 | 17.3 | 36.0 | 48.7 | 35.6 | 25.0 | 8.4 |
| $4^{th}$ 20 puffs | 2.0 | 19.2 | 38.1 | 46.7 | 30.6 | 22.9 | 5.4 |
| $5^{th}$ 20 puffs | 2.0 | 14.4 | 37.8 | 36.8 | 30.4 | 22.4 | 4.4 |
| Mean Nicotine (in 100 puffs) μg/puff ± SD | 3.24 ± 2.3 | 20.97 ± 7.2 | 38.86 ± 1.9 | 43.42 ± 5.5 | 34.85 ± 4.2 | 28.92 ± 8.7 | 11.98 ± 9.7 |

Discussion:

The results of Experiment 7 demonstrate the nicotine aerosol delivery with different proportion of potassium hydroxide to nicotine base in water. It is remarkable to note that the sustained enhancement in nicotine delivery achieved in nicotine and potassium hydroxide ratio of 10:40, 10:60, 10:80 and 10:100 while the 10:60 ratio appears superior to the other three. Hence, by adjusting the ratio of potassium hydroxide concentration to nicotine base, the nicotine aerosol delivery can be controlled to the optimum level as needed. The pH measured higher with each increased amount of potassium hydroxide. Thus more alkaline pH per se was not correlated with nicotine delivery The greater delivery of nicotine at intermediate concentrations of KOH was instead correlated with the appearance of an emulsion consisting of small globules of nicotine suspended in the aqueous solution of KOH. Low concentrations of KOH (e.g. 10 mg KOH in 200 microliters of water) were insufficient to induce this phase separation. Very high concentrations (e.g., 200 mg KOH in 200 microliters of water), while inducing a phase separation, did not stabilize the nicotine-in-KOH solution emulsion consisting of small globules of nicotine surrounded by KOH solution. Instead, a continuous layer of nicotine was formed, possibly due to the increasing surface tension of highly concentrated aqueous solutions of KOH (P M Dunlap and S R Faris, Surface Tension of Aqueous Solutions of Potassium Hydroxide, Nature 196, 1312-1313, 1962). Without a stable emulsion, the enhancement in nicotine yield over many puffs, was not seen under the conditions tested. That is, the enhancement of nicotine delivery may depend on sequestration of pyruvic acid in the KOH solution surrounding small nicotine-containing globules.

Experiment #8: Screening of Additional Chemicals to Generate and Deliver Efficient Nicotine Pyruvate Aerosol Objective:

The aim of the current was to explore some additional chemicals (preferably alkali metal hydroxides/oxides and alkaline earth metal hydroxides/oxides) and salts in addition to potassium hydroxide to generate and deliver sustainable amount of nicotine pyruvate aerosol.

Materials and Methods
Nicotine Base Solution:

About 10 μL (10 mg) of nicotine base was mixed with 300 μL of water which contained 100 mg of the selected base and salt in side arm test tube (Nicotine unit). The nicotine units were kept at room temperature for an hour (to cool down if there was any exothermic heat) prior to the experiments. The following list of candidates was screened for their ability to enhance sustainable nicotine aerosol delivery.

Alkali Metal Hydroxides and Oxides:
Potassium hydroxide (KOH)
Potassium tertiary butoxide [$(CH_3)_3COK$]
Potassium superoxide ($KO_2$)
Sodium hydroxide (NaOH)
Sodium butoxide [$CH_3(CH_2)_3ONa$]
Sodium tertiary butoxide [$(CH_3)_3CONa$]
Lithium oxide ($Li_2O$)
Alkaline Earth Metal Oxides:
Calcium oxide (CaO)
Beryllium oxide (BeO)
Barium oxide (BaO)
Barium peroxide ($BaO_2$)
Salts:
Potassium chloride (KCl)
Sodium chloride (NaCl)
Sodium carbonate ($Na_2CO_3$)
Sodium citrate [$HOC(COONa)(CH_2COONa)_2$]
Ammonium sulfate [$(NH_4)_2SO_4$]

Pyruvic Acid:

About 1 mL of pyruvic acid (PA) was measured into a side arm glass test tube for each experiment and the air flow was introduced through a Pasteur pipette (Pyruvic acid unit).

Testing Procedure:

The nicotine unit was connected to the pyruvic acid unit and the aerosol samples were collected as per the method described in Experiment #1.

Results:

The samples were analyzed for nicotine content and the mean amount of nicotine delivered in each 60 puffs of aerosol is furnished in Table 11.

TABLE 11

Nicotine delivery when pyruvic acid vapor passed over some alkali metal hydroxides/oxides, alkaline earth metal oxides and salts mixture of nicotine at room temperature

| Sample ID | Mean Nicotine (µg)/puff | Post experimental pH |
|---|---|---|
| ALKALI METAL HYDROXIDES AND OXIDES | | |
| PA over nicotine + potassium hydroxide | 41.04 | 14.2 |
| PA over nicotine + sodium hydroxide | 28.87 | 11.0 |
| PA over nicotine + lithium oxide | 36.01 | 11.5 |
| ALKALINE EARTH METAL OXIDES | | |
| PA over nicotine + barium oxide | 14.18 | 13.3 |
| SALTS | | |
| PA over nicotine + potassium chloride | 16.50 | 08.9 |
| PA over nicotine + sodium chloride | 19.20 | 08.4 |
| PA over nicotine + sodium carbonate | 13.98 | 10.8 |
| PA over nicotine + sodium citrate | 11.56 | 08.5 |
| PA over nicotine + ammonium sulfate | 21.22 | 05.2 |
| CONTROLS | | |
| PA over nicotine (10 µL) + water (300 µL) | 00.41 | 08.0 |
| PA over nicotine (10 µL) | 25.62 | 08.0 |

Discussion:

The results of Experiment 8 clearly exhibit that the alkali metals (potassium, sodium and lithium) hydroxides/oxides are the most efficient group in order to generate and deliver sustainable and enhanced amount of nicotine in aerosol when compared to the alkaline earth metals (beryllium, calcium and barium) oxides. Among the tested alkali metals hydroxides/oxides, the potassium and lithium hydroxide/oxides are confirmed to be the superior candidates to deliver enhanced nicotine delivery in the aerosol.

Furthermore, the nicotine aerosol delivered in the experiments in which the salt solutions were mixed with nicotine base was found to yield an interesting outcome. Although the control experiment (without any water, salt or alkali metal hydroxides/oxide and alkaline earth metal oxides) has delivered about 25.62 µg/puff of nicotine in aerosol, mixing the selected salt solutions with nicotine base could prove advantageous in enhancing the nicotine delivery in the aerosol when compared to the control experimental result, for two reasons:

1) Nicotine is known to form an azeotrope with water which may be resolved into separate nicotine and water phases within certain ranges of nicotine concentration and temperature. C. S. Hudson, Zeit. Phys. Chem., 47, 113 (1904). By causing a separation of nicotine from an azeotropic aqueous solution as seen in Experiment #7 above, the delivery of nicotine will be enhanced compared to nicotine diluted in the same volume of water; and 2) by allowing the use of a larger solution volume than with pure nicotine base, the solution might be spread over a larger surface area, promoting more effective volatilization of nicotine.

Without intending to be bound by any particular theory of mechanism, the increased nicotine vapor from aqueous nicotine solutions with, e.g., KCl and KOH seen above, may represent the effects of electrolytes "salting out" the nicotine base from solution. In industrial chemistry, this would correspond in concept to salt-effect distillations such as the use of potassium acetate in separating azeotropic mixes of water and ethanol. Schmit, D., Vogelpohl, A. (1983). Distillation of ethanol-water solutions in the presence of potassium acetate. Separation Science and Technology, 18 (6), 547-554. In general, this salting out effect should be most effective where the electrolytes have highly divergent solubilities in nicotine base and water, with high solubility in water and low solubility in nicotine base. The technology developed in the bioethanol production area for salt effect distillation of ethanol from aqueous azeotropic mixtures provides an analytical framework for evaluating other salts in addition to those tested herein. R. T. P. Pinto, M. R. Wolf-Maciel, L. Lintomen, Saline extractive distillation process for ethanol purification, Computers & Chemical Engineering, Volume 24, Issues 2-7, 15 Jul. 2000, Pages 1689-1694; Mario Llano-Restrepo, Jaime Aguilar-Arias, Modeling and simulation of saline extractive distillation columns for the production of absolute ethanol, Computers & Chemical Engineering, Volume 27, Issue 4, 15 Apr. 2003, Pages 527-549.

Figure 16:
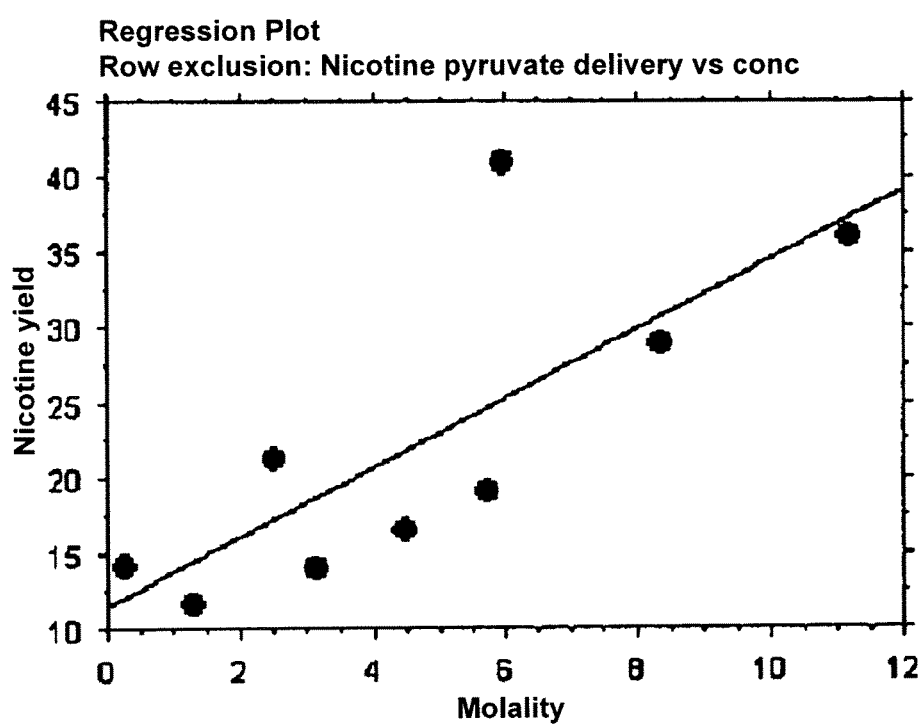
FIG. 16 is a graphical representation illustrating a regression plot of Molality vs. Nicotine yield.

We tested the dependence of nicotine aerosolization on concentration by calculating the molalities of the solutions of the substances in Table 11. FIG. 16 illustrates a graph demonstrating that there is a good correlation (correlation coefficient r=0.76 and p value=0.016). For comparison, insoluble compounds such as beryllium oxide or calcium oxide did not improve nicotine delivery over the control aqueous solution (data not shown). Other electrolyte forming compounds tested included potassium tertiary butoxide, potassium superoxide, sodium butoxide, sodium tertiary butoxide, and barium peroxide.

In addition to the salting out effect, mild heating is well established as inducing a shift to a two phase nicotine and water state. C. S. Hudson, Zeit. Phys. Chem., 47, 113 (1904). Sufficient increases in ionic strength may alter the phase shift temperature to require a lower degree of heating or even no heating at all to induce this shift.

Heating the salted out mixture would further correspond in concept to the salt effect distillations discussed above. This is consistent with the general trend of higher initial nicotine delivery for strong bases (KOH, NaOH) verses salts (KCl, NaCl). Thus, electrolyte producing compounds that are exothermic upon dissolution in water are preferred in certain embodiments.

In embodiments where the Delivery Enhancing Compound is an acid such as pyruvic acid, the acid may over time dissolve into the nicotine source and acidify it. This acidification is associated with a decreased nicotine delivery over time, possibly due to the neutralization of nicotine base (pKa of protonated nicotine is 8.5). Thus, in these embodiments, preferred electrolyte producing compounds are exothermic upon dissolution in water and additionally are strong bases (i.e. they yield a nicotine/water pH of >11, 12, 13 or 14). An especially preferred species in this regard is KOH.

Exemplary Devices Adapted for Use with the Methods Herein

Delivery devices of some embodiments comprise a housing which simulates a tobacco smoking article. The housing may simulate the size, shape, and/or configuration of any article used for smoking tobacco articles. Non-limiting examples of smoking articles according to the present invention include cigarettes, cigars, cigarillos and pipes.

Delivery devices of some embodiments comprise a housing which simulates a pharmaceutical inhalation device. The housing may simulate the size, shape, and/or configuration of any pharmaceutical device used for inhalation. Non-limiting examples of pharmaceutical inhalation devices according to the present invention include, metered dose inhalers, pressurized metered dose inhalers, dry powder inhalers, nebulizers and liquid based inhalers.

Exemplary Device 1

Directing attention to FIG. 1, a device for the formation and delivery of a nicotine aerosol to a user according to an embodiment of the present invention is shown. Specifically, nicotine inhaler 10 having the size, shape, and appearance of a cigarette is shown. Nicotine inhaler 10 consists of housing 12, which has an elongated cylindrical shape and is hollow. To allow for a gaseous flow through inhaler 10, housing 12 contains gaseous inlet 14 and gaseous outlet 16 on opposing ends.

The portion of housing 12 between gaseous inlet 14 and gaseous outlet 16 is divided into three compartments capable of holding a first, second, and/or third substance. The first, second, or third substance can comprise a vapor forming medicament, such as nicotine.

Figure 2:
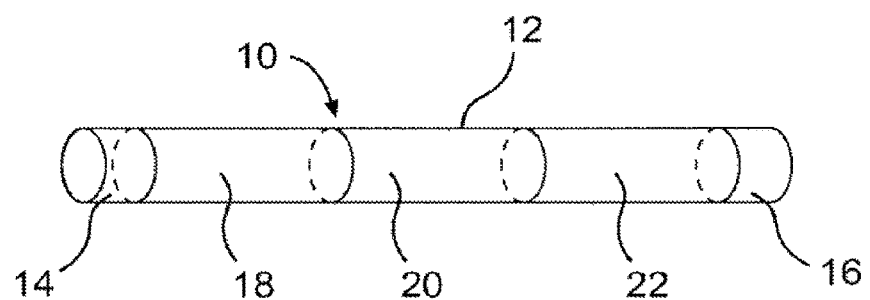
FIG. 2 a perspective view of the interior of an exemplary delivery device simulating a cigarette.

As illustrated in FIG. 2, nicotine inhaler 10 includes first compartment 18, second compartment 20, and third compartment 22. Nicotine, preferably in the free base form, may be placed in any of the three compartments. For example, nicotine can be placed within second compartment 20. A suitable delivery enhancing compound, such as an acid, is placed within first compartment 18. Any suitable acid can be used. For example, pyruvic acid can be placed within first compartment 18. Pyruvic acid is a volatile substance which has a substantial vapor pressure at room temperature. As such, any free space within first compartment 18 will be filled to some degree with pyruvic acid vapor, that is, gaseous pyruvic acid. Although the vapor pressure of nicotine is less than that of pyruvic acid, nicotine is also a volatile substance. In the same manner, any free space within second compartment 20 will be filled to some degree with nicotine vapor.

It should be appreciated that the pyruvic acid is held within first compartment 18 on a delivery enhancing compound source element (not shown) and nicotine is held within second compartment 20 on a nicotine source element (not shown). Additionally, a third substance may be held on a third source element (not shown) within third compartment 22. Furthermore, one or more of the source elements may be integral with or part of compartments 18, 20, and 22, respectively.

The delivery enhancing compound source element can be any size and shape that allows a gaseous stream to contact a vapor of the acid and pass through first compartment 18. The nicotine source element can be any size and shape that allows a gaseous stream to contact a vapor of nicotine and pass through second compartment 20. The third source element can be any size and shape that allows a gaseous stream to contact a third substance and pass through third compartment 22.

The delivery enhancing compound source element can be composed of any suitable material capable of holding the acid on its surface while allowing the acid vapors to escape into the surrounding area. The nicotine source element can be composed of any suitable material capable of holding nicotine on its surface while allowing the nicotine vapors to escape into the surrounding area. The third source element can be composed of any suitable material capable of holding a third substance. In specific embodiments, the suitable material holds the third substance on its surface while allowing the vapor of the third substance to escape into the surrounding area.

Preferably, a suitable source element material is inert to any substance to be placed on its surface. Additionally, a suitable material is preferably adsorbing with respect to any substance to be placed on its surface such that said substance is adsorbed on the surface of the material. Although a material having both absorptive and adsorptive characteristics can be employed, a material capable of holding the delivery enhancing compound(s), nicotine and/or third substance through adsorption is preferred. Non-limiting examples include glass, aluminum, PET, PBT, PTFE, ePTFE, and BAREX®, preferably in the form of a fibrous network.

The adsorptive material may function via capillary action to continuously present the substances to the surface of the adsorbing material.

Third compartment 22 can contain a purifying agent. For example, activated charcoal can be incorporated into third compartment 22 using any method which provides the resulting third compartment 22 with gas purification capability. Suitable methods are well-known in the art. For example, the charcoal may be placed within third compartment 22 as a charcoal plug or filter.

Figure 3:
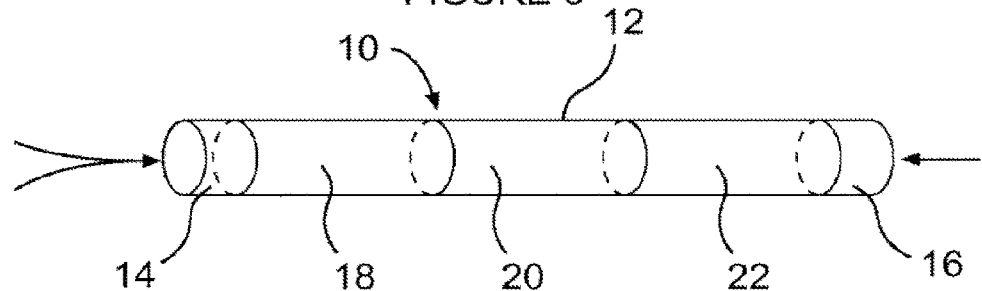
FIG. 3 a perspective view of the exemplary delivery device from FIGS. 1 and 2 in use.

In operation, a user puffs on gaseous outlet 16 of nicotine inhaler 10, as shown in FIG. 3. The partial vacuum created by the puffing action draws a gaseous stream into housing 12 through gaseous inlet 14. The gaseous stream enters first compartment 18 and captures a vapor of the acid by passing over the pyruvic acid source element held in first compartment 18. The gaseous stream that exits first compartment 18 and subsequently enters second compartment 20 is an acid-containing gaseous stream. The acid-containing gaseous stream generates a stream of nicotine-containing particles by passing over the nicotine held by the nicotine source element in second compartment 20. The stream of nicotine-containing particles passes through third compartment 22 and exits through gaseous outlet 16 into the mouth of the user. Any unreacted acid is removed from the stream of nicotine-containing particles via the activated charcoal filter in third compartment 22. It should be appreciated that pyruvic acid could be held on a first element in first compartment 18 and/or nicotine could be held on a second element in second compartment 20. Additionally, a third substance, such as a purifying or flavoring agent, may be held on a third element in third compartment 22. Furthermore, the first, second, and third elements may be integral with or part of compartments 18, 20, and 22, respectively.

Exemplary Device 2

Figure 4:
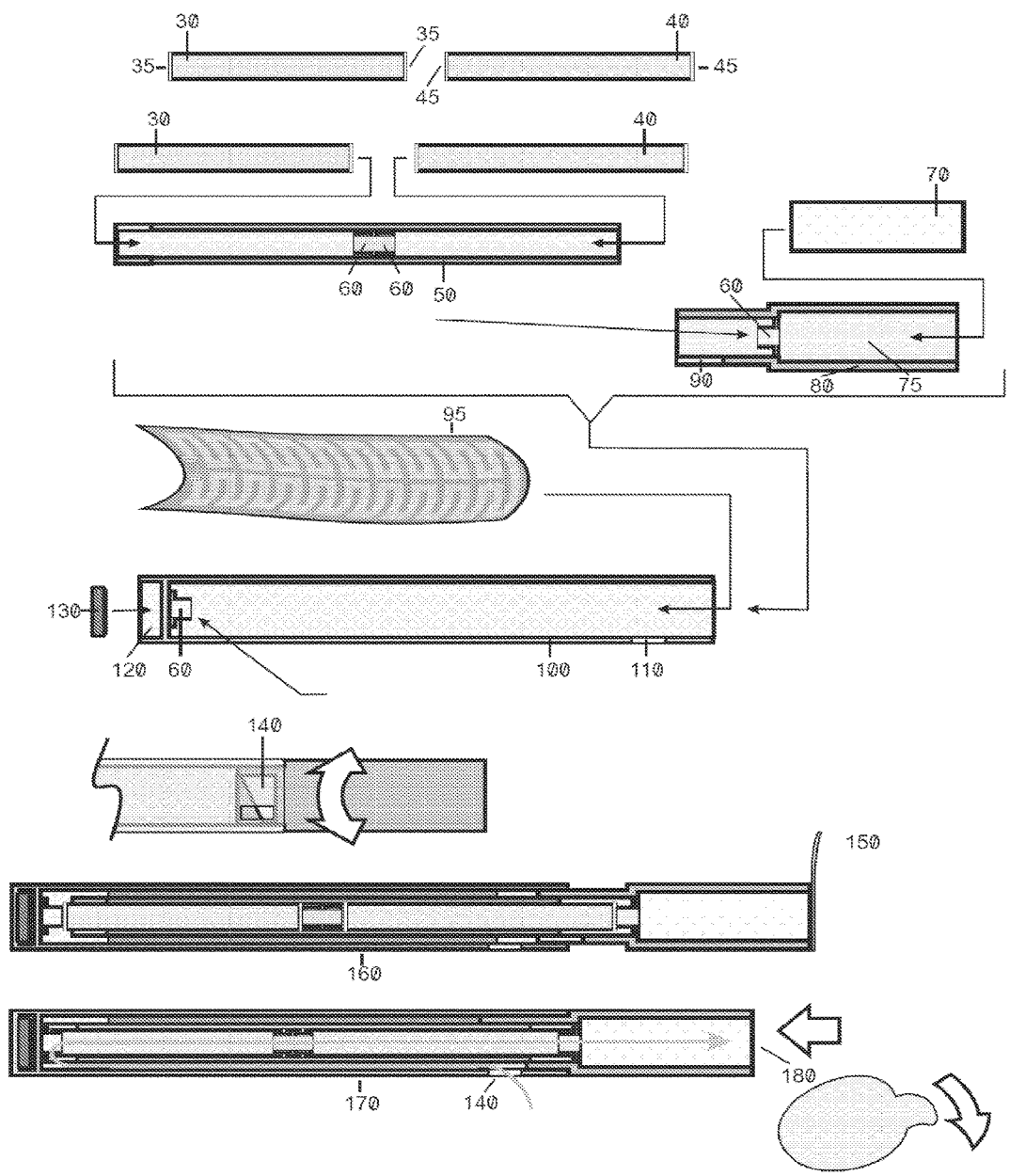
FIG. 4 a sectional view of the subcomponents of an exemplary delivery device showing the assembly stages and final configuration of the components for device use.

This exemplary device is illustrated and described by reference to FIGS. 4-6. In FIG. 4, the elements of the device are shown in an assembly flow chart. The delivery enhancing compound source 30 and the nicotine source 40 are optionally manufactured and stored as independent components generally having frangible barrier end caps 35 and 45 heat sealed on the ends. These two elements 30 and 40 are inserted into a first housing 50. First housing 50, containing delivery enhancing compound source 30 and the nicotine source 40, is then inserted into a second housing 100. The housings 50 and 100 and the elements 30 and 40 are generally extruded plastic tubing. Also inserted into second housing 100 is heating element 95. The heating element 95 is generally a thin flexible heating foil which is configured to wrap around housing 50 and to contact housing 50 sufficiently to enable heating the delivery enhancing compound source 30 and/or the nicotine source 40 to a desired temperature (e.g. 40 degrees C.). Heating element 95 is also adapted to contact battery 130 to supply power to the heating foil element 95.

Filter element 80 is adapted to slidably insert and snap-lock into second housing 100. Filter element 80 comprises as filter cavity 75 adapted to contain a filter 70. Filter 70 is generally a charcoal filter and may contain additional volatile compounds such as flavoring agents commonly used in cigarettes. Filter element 80 may have foil seal 150 to seal the assembled pre-use configuration 160.

Filter element 80 has aperture 90 which aligns with aperture 110 of second housing 100. As assembled, air inlet 140 is formed. The filter element 80 and the second housing 100 are configured to permit slidable rotation to select a desired air inlet 140 aperture dimension. The air inlet 140 forms when filter element 80 is fully inserted into second housing 100 as shown by 170. The full insertion of filter element 80 also forces penetrating elements 60 through frangible barriers 35 and 45 to unseal these elements for an unobstructed air flow pathway from air inlet 140 to particle delivery aperture 180.

Figure 5:
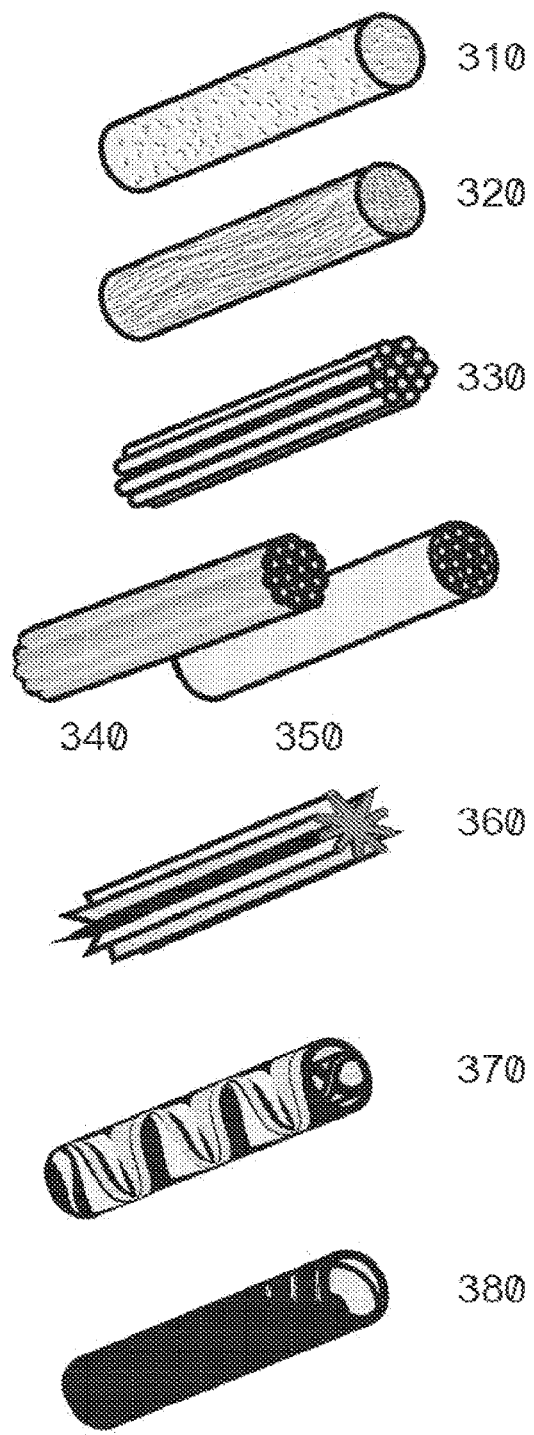
FIG. 5 a perspective view of various source elements for providing the nicotine or other medicament and the delivery enhancing compound.

FIG. 5 shows various alternative structures for delivery enhancing compound source 30 and the nicotine source 40. The delivery enhancing compound in this configuration is generally a volatile acid which may be held by adsorption onto sintered plug 310, PE wick 320, a fiber bundle 330, a multilumen tube 340 or 350, woven or non-woven PET, PBT, or PETG fabric material 360, PET static mixer 370, or a helical path wrapped in nonwoven material 380.

Figure 6:
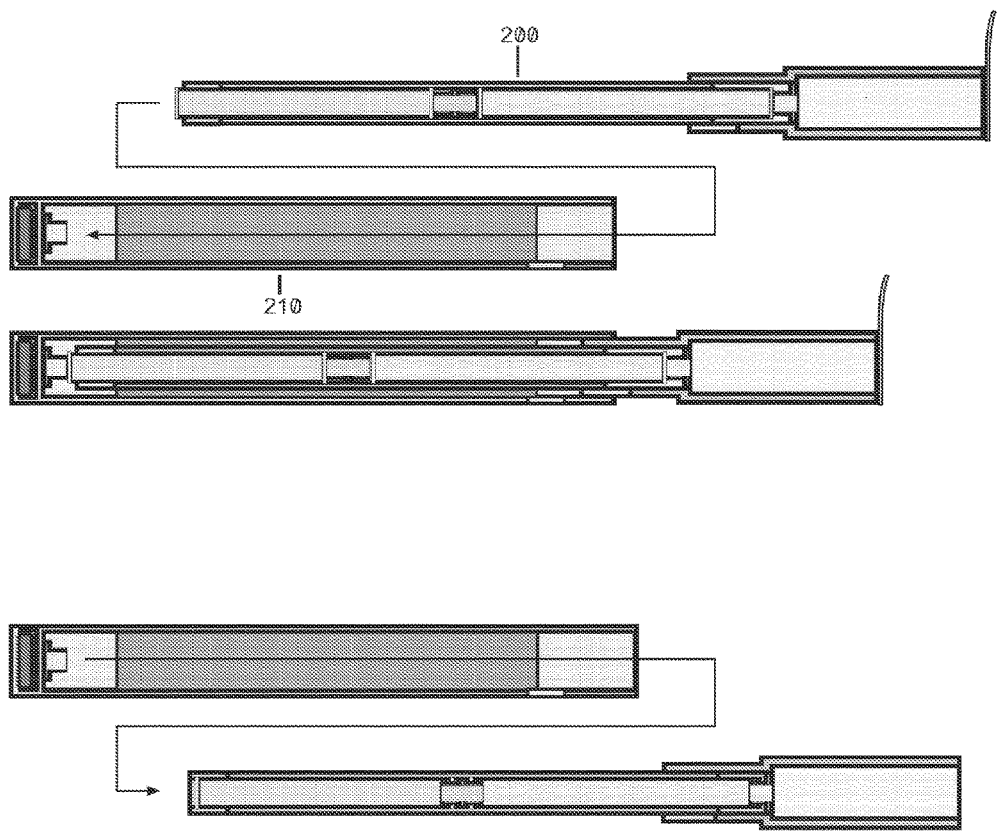
FIG. 6 a sectional view of the subcomponents of an exemplary delivery device showing reusable and disposable portions.

FIG. 6 shows some embodiments of this device where the device comprises a reusable portion 210 and a disposable portion 200. Referring to FIG. 1, disposable portion 200 comprises the delivery enhancing compound source 30 and the nicotine source 40, the first housing 50, and the filter element 80. The reusable portion 210 comprises second housing 100, heating element 95 and battery 130.

Exemplary Device 3

Figure 7:
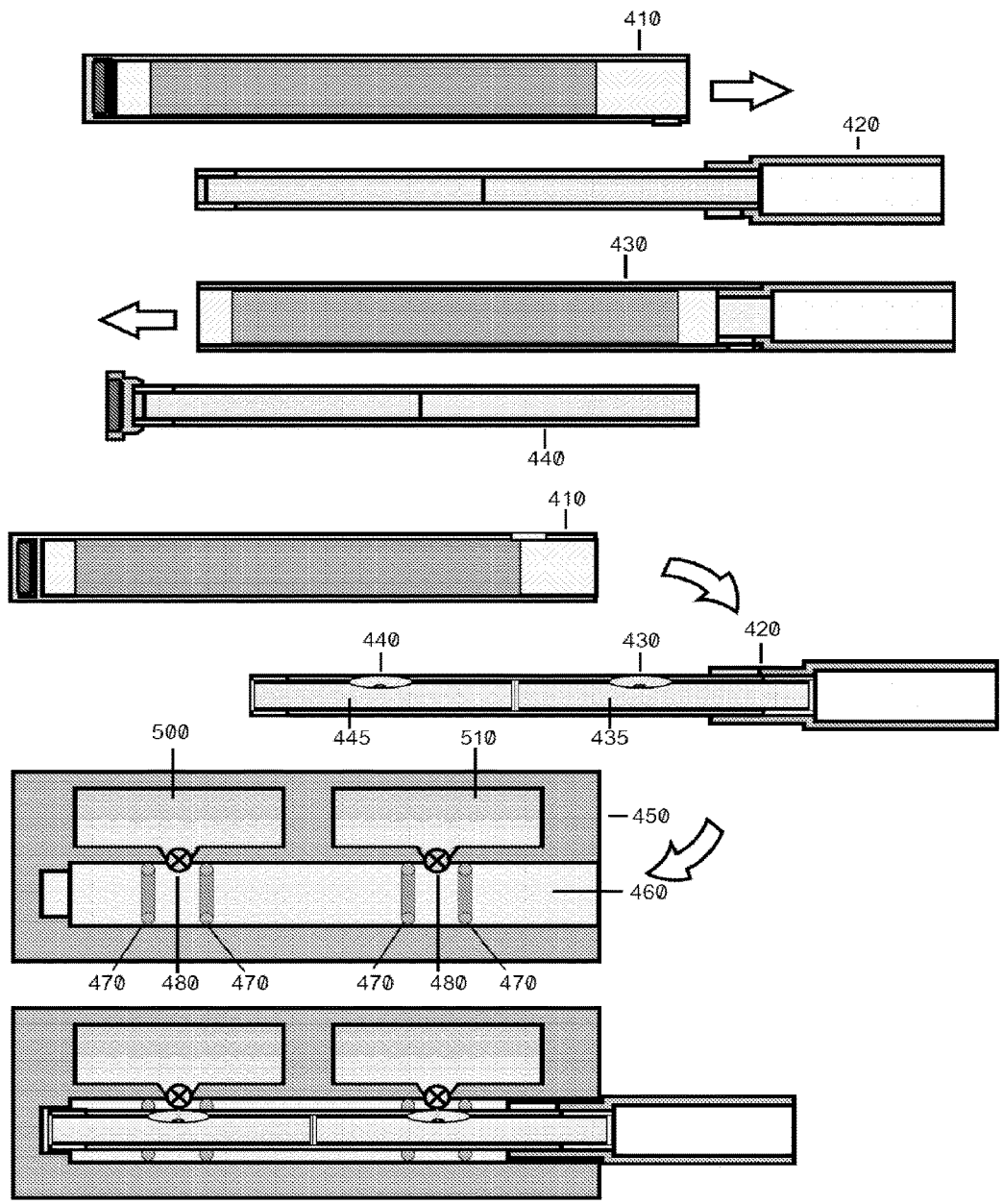
FIG. 7 a sectional view of the subcomponents of a reusable exemplary delivery device showing the device and a recharging unit for supplying nicotine or other medicament and the delivery enhancing compound.

A fully reusable exemplary device is illustrated by FIG. 7. Two alternative configurations are illustrated wherein portion 410 and 420 or 430 and 440 are reversibly attachable. For example the portions may be extruded plastic adapted and dimensioned to permit repeated snap-locking and removal. The removable portions 420 or 440 comprise apertures 430 and 440 for communication with delivery enhancing compound source 445 and nicotine source 435. Portions 420 or 440 slidably insert into recharging element 450 through aperture 460. Elements 470 are sealing o-rings to seal off the reservoir when recharging delivery enhancing compound source 445 and nicotine source 435. Loading apertures 480 and 490 are configured to communicate with delivery enhancing compound source 445 and nicotine source 435 once portion 420 is seated in recharging element 450. In some embodiments, gravity drives flow from delivery enhancing compound reservoir 500 and nicotine reservoir 510 to delivery enhancing compound source 445 and nicotine source 435, respectively. In some embodiments, the flow from the reservoirs to the sources is in part due to wicking of the reservoir liquid by the source elements. For example, delivery enhancing compound source 445 and nicotine source 435 may comprise a source element containing PET to create rapid wicking and thus reloading of sources 445 and 435.

Exemplary Device 4

Figure 8:
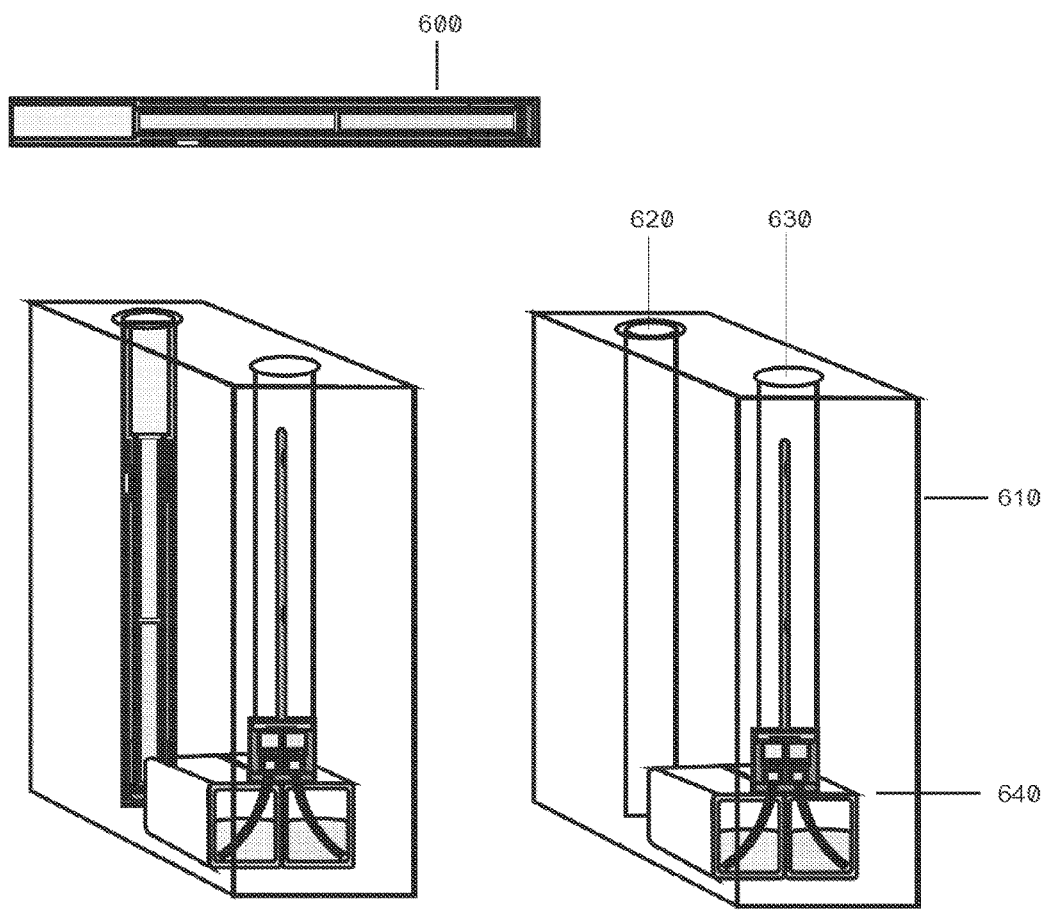
FIG. 8 a sectional view of a reusable exemplary delivery device showing the device and a perspective view a recharging unit for supplying nicotine or other medicament and the delivery enhancing compound.
Figure 9:
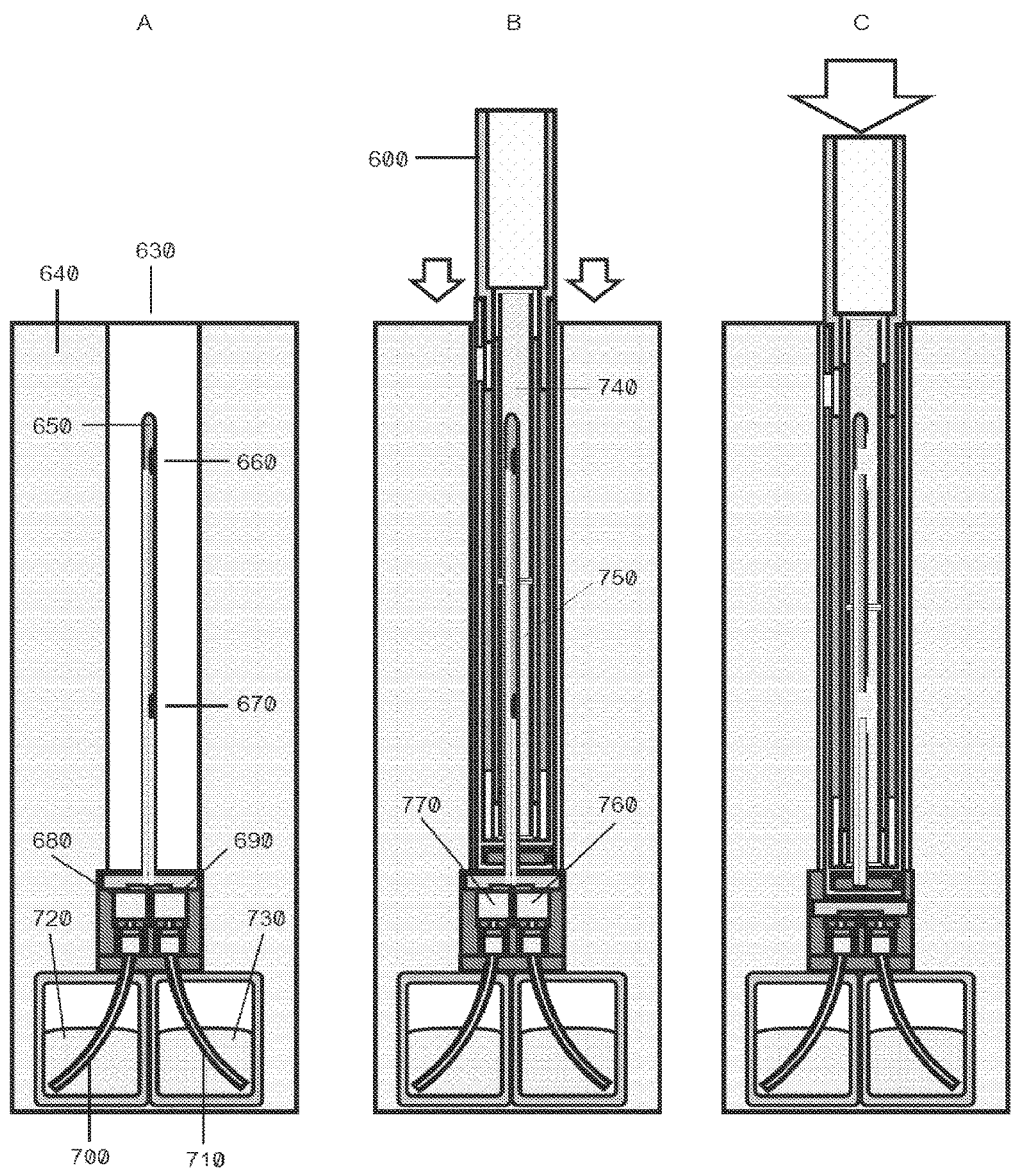
FIG. 9 a sectional view of a reusable exemplary delivery device showing the device and a recharging unit; 9A shows the recharging unit alone, 9B shows the delivery device seated in the recharging unit and 9C shows the delivery device after compression of the metered dose pumps of the recharging unit for resupplying nicotine or other medicament and the delivery enhancing compound.

Another exemplary device is illustrated by FIGS. 8 and 9. This exemplary device is rechargeable and configured to simulate a typical cigarette pack. Referring to FIG. 8, delivery device 600 is configured to insert into recharging unit 610 through storage aperture 620 and recharging aperture 630. When fully seated in the recharging unit 610 on recharging element 640, the device 600 is recharged with delivery enhancing compound and/or nicotine.

FIG. 9 shows a detailed the recharging element 640 in detail. In FIG. 9A, injection element 650 having loading apertures 660 and 670 is in flow communication with reservoirs 720 and 730 through metered dose actuator pumps 680 and 690 and tubes 700 and 710. In FIG. 9B, delivery device 600 is shown seated in recharging unit 640. Injection element 650 passes through a recharging aperture at the base of the delivery device and into said device so that apertures 660 and 670 are in communication with nicotine source element 740 and delivery enhancing compound source element 750. In FIG. 9C, the delivery device 600 is further inserted into recharging unit 640 to actuate the pumps 680 and 690 to deliver metered doses 770 of nicotine and 760 of delivery enhancing compound through apertures 660 and 670, respectively, and into nicotine source element 740 and delivery enhancing compound source element 750, respectively.

Exemplary Device 5

Figure 10:
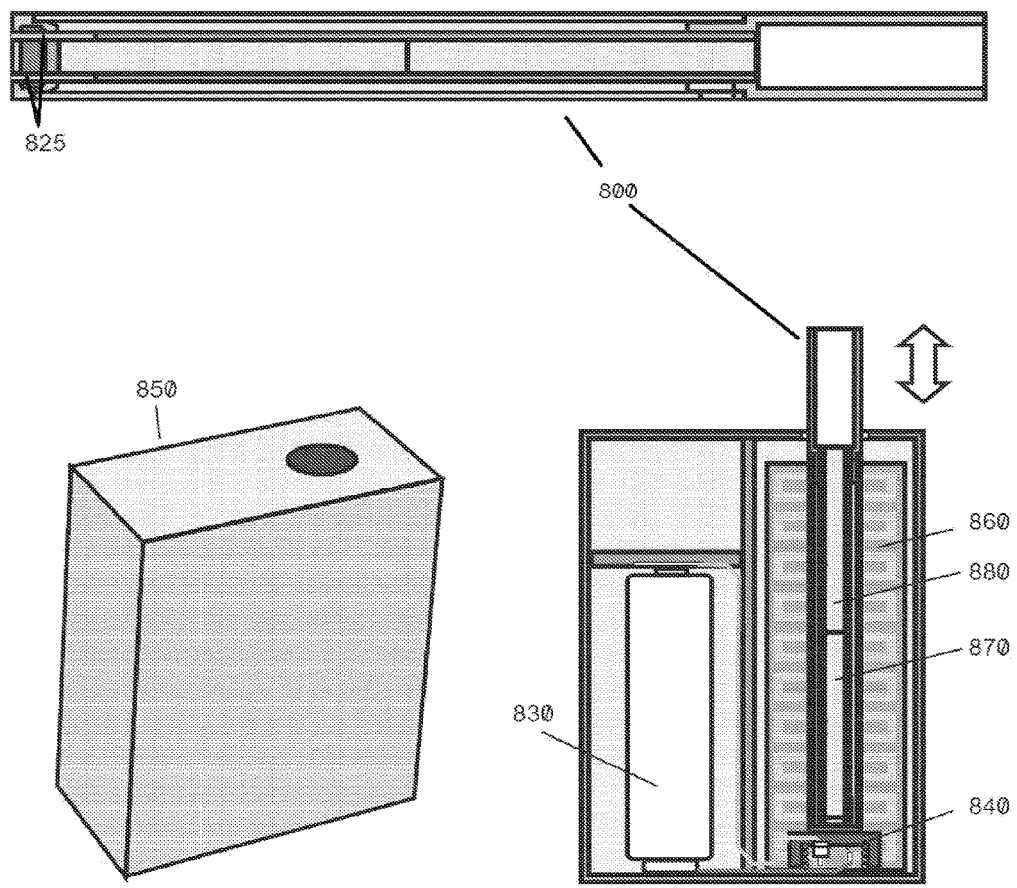
FIG. 10A a sectional view of an exemplary delivery device with a heating component therein shown in perspective view as a separate component; 10B an exemplary delivery device having an external heating unit into which the delivery device is seated for temperature control of the device and/or its constituents.

This exemplary device is illustrated by FIG. 10. This device configuration has a heating unit 850 external to the delivery device 800. Upon insertion of delivery device 800 into heating unit 850, electrical contacts 840 are in contact with leads 825 which permit battery 830 to heat foil heating element 860 to control the temperature of the delivery enhancing compound source 870 and nicotine source 880 to, e.g., 40±5 degrees C. An alternative configuration places the heating foil 860 within the delivery device 800, as shown in FIG. 4.

Exemplary Device 6

Figure 11:
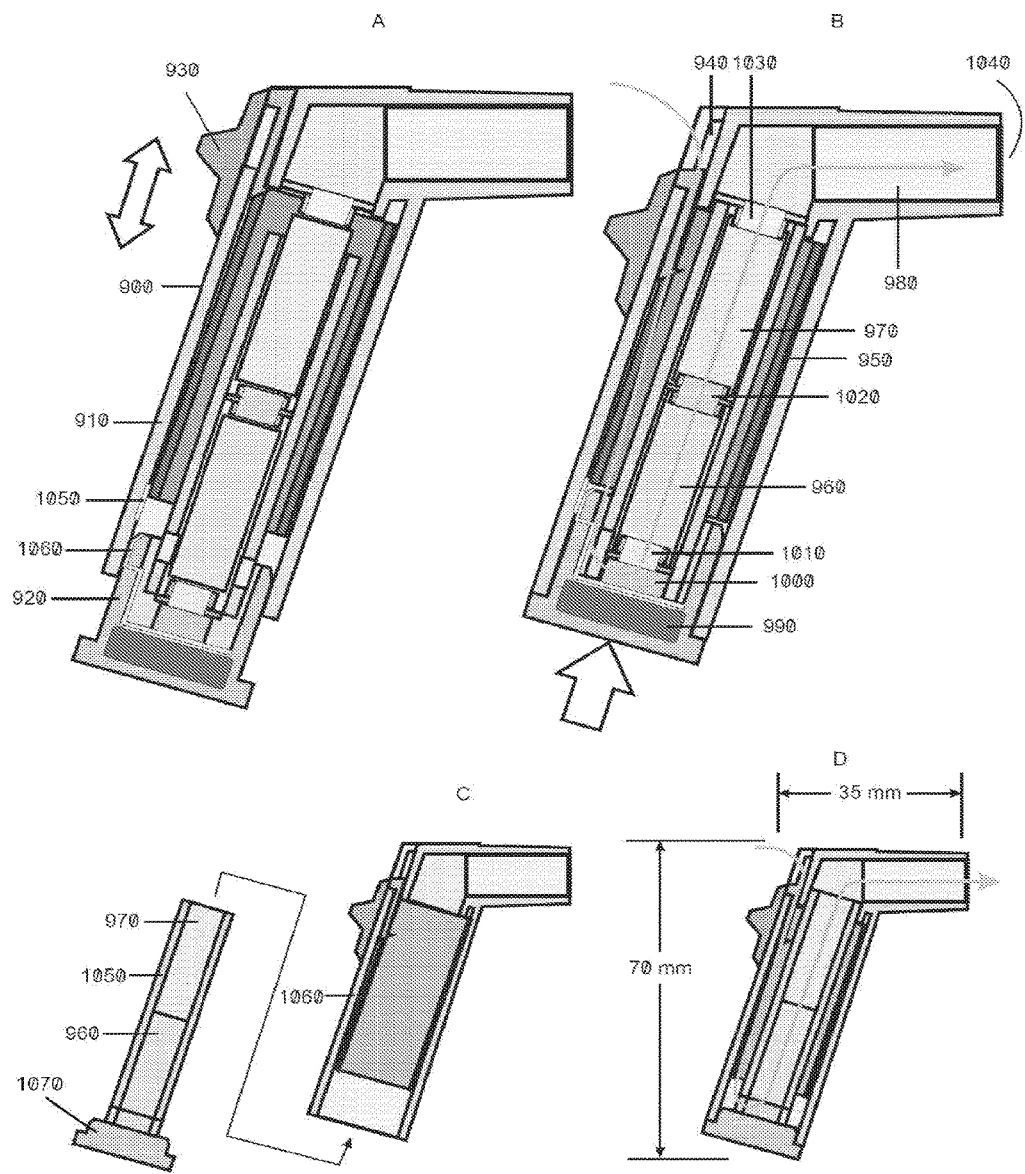
FIG. 11 a sectional view of an exemplary device simulates a metered dose inhaler commonly used for pharmaceutical delivery of inhaled medicaments.

The foregoing exemplary devices are generally configured to simulate a cigarette and cigarette pack. The delivery devices suitable for use with the methods herein are readily configured in a variety of ways. An example is illustrated in FIG. 11. This exemplary device simulates a metered dose inhaler commonly used for pharmaceutical delivery of inhaled medicaments. Delivery device 900 comprises a first housing 910 and a second housing 920. Second housing 920 is slidable out (FIG. 11A) and in (FIG. 11B) for recharging or replacement of battery 990. The in position brings electrical contact 1050 and 1060 into communication thereby allowing battery 990 to heat foil heating element 950 to in turn control the temperature of delivery enhancing compound source 960 and nicotine source 970. Air intake actuator 930 is configured to slide anywhere from the position in FIGS. 11A to 11B. Power for heating foil element 950 may be optionally turned on or off using air intake actuator 930 or a separate switching means (not shown). Air intake aperture 940 may then be opened to a selected degree thereby controlling the volume of air per inhalation and consequently the amount of nicotine. This feature is analogous to adjustable air intake aperture 140 of FIG. 1. In operation, air is drawn through air intake aperture 940, down to chamber 1000, through conduit 1010, through the delivery enhancing compound source 960 where delivery enhancing compound is captured in the air flow. For example, pyruvic acid vapor may be emanating from a PET source element having liquid pyruvic acid adsorbed thereon. This vapor is moved by the air flow through conduit 1020 into the nicotine source 970. Here the delivery enhancing compound increases the concentration of nicotine in the airflow relative to the amount of nicotine vapor that would be contained in the same volume of air flow in the absence of the delivery enhancing compound. In the case of pyruvic acid, nicotine pyruvate salt particulates may be formed to enhance delivery of nicotine to a subject. Delivery may be further enhanced by elevating the temperature of, e.g., pyruvic acid and nicotine, by means of heating element 950 to increase the vapor pressure of those compounds. The airflow containing nicotine now moves through conduit 1030, through charcoal filter 980 and out the inhalation aperture 1040.

FIGS. 11 C and D illustrate an embodiment of the exemplary inhaler device 900 wherein a portion of the device having the delivery enhancing compound source 960 and nicotine source 970 in a disposable housing 1050 which is configured to slide into and out of reusable housing 1060 to form a device functionally identical to device 900. Battery housing element 1070 is detachable from disposable element 1050 and thus reusable with portion 1060 and a replacement element 1050.

Exemplary Device 7

Figure 12:
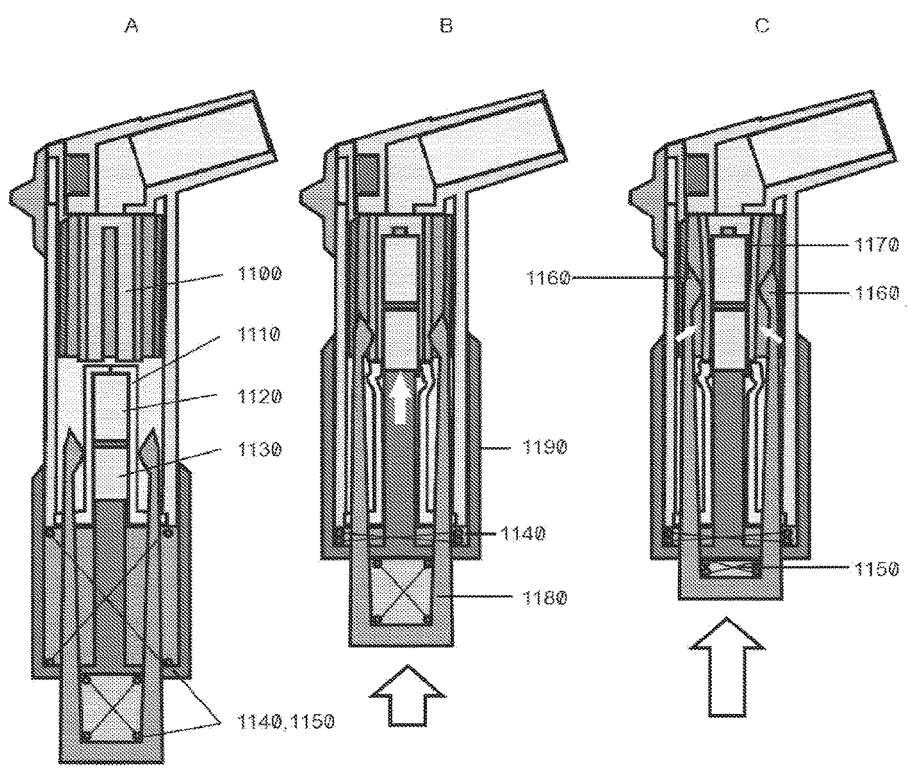
FIG. 12 a sectional view of an exemplary device simulates a metered dose inhaler commonly used for pharmaceutical delivery of inhaled medicaments.

FIG. 12, A-C illustrates another configuration of an inhalation device. In this configuration, the delivery enhancing compound source and the nicotine source are the lower and upper surface areas of split inner tube 1100. In the usage configuration 12A, an impermeable cover 1110 is in place over nicotine reservoir 1120 and delivery enhancing compound reservoir 1130. The impermeable cover 1110 reduces evaporative loss from the reservoirs and physically separates the reservoirs from the split inner tube 1100. In use, slidable bottom housing 1180 is pushed into main housing 1190 until first catch spring 1140 is locked in the position shown in 12B. This places the reservoirs 1120 and 1130 in parallel proximity to the split inner tube 1100. Shown in 9C, the bottom housing 1180 is further inserted into main housing 1190 until second catch spring 1150 is locked in the position shown in 12C. In this third position, pressure elements 1160 squeeze split inner tube 1100 to force wall 1170 into contact with reservoirs 1120 and 1130. This action forces nicotine and delivery enhancing compound (e.g. pyruvic acid) onto the inner surface of wall 1170 to recharge this surface as the nicotine source and the delivery enhancing compound source.

Exemplary Device 8

Figure 13:
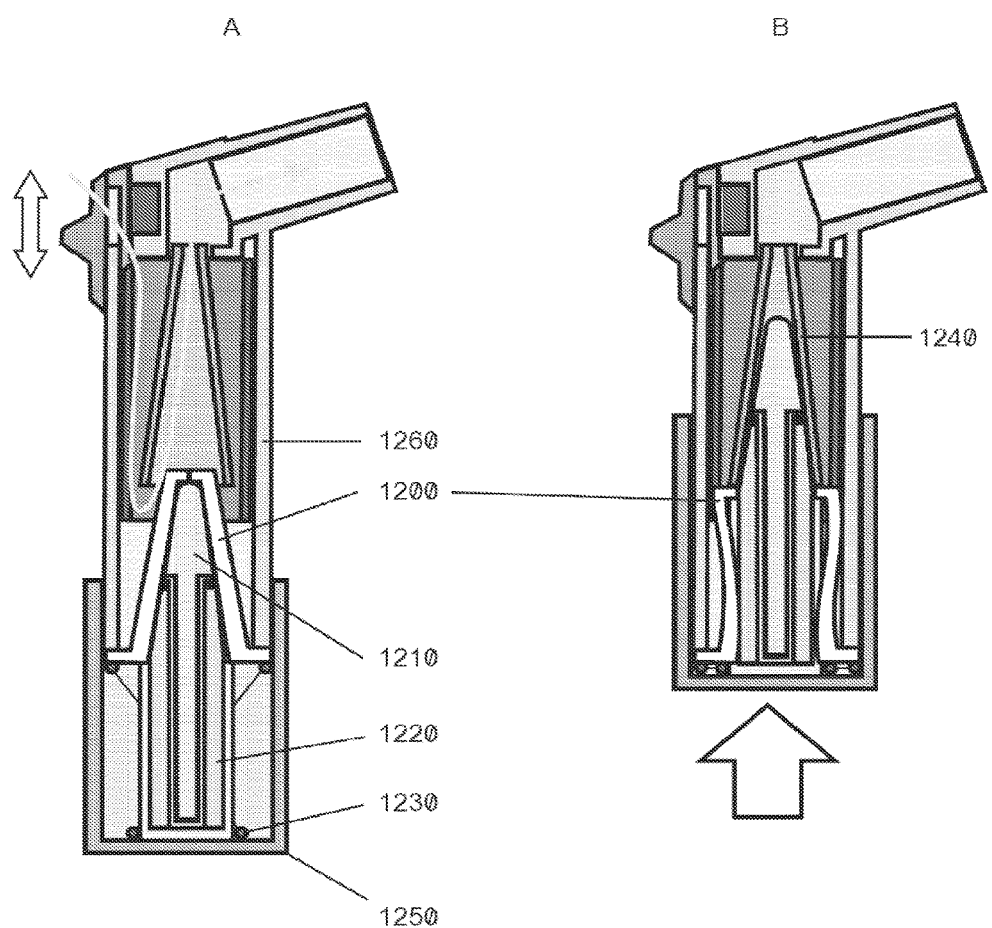
FIG. 13 a sectional view of an exemplary device simulates a metered dose inhaler commonly used for pharmaceutical delivery of inhaled medicaments.

FIG. 13 shows a variant of the device of FIG. 12. In this version, bottom housing 1250 is depressed against conical spring 1230 to force the nicotine reservoir 1210 and the delivery enhancing compound reservoir 1220 through reservoir cover 1200 and into contact with the inner surface of conical inner tube 1240, thereby coating the surface with nicotine and delivery enhancing compound (FIG. 13B).

Exemplary Device 9

Figure 14:
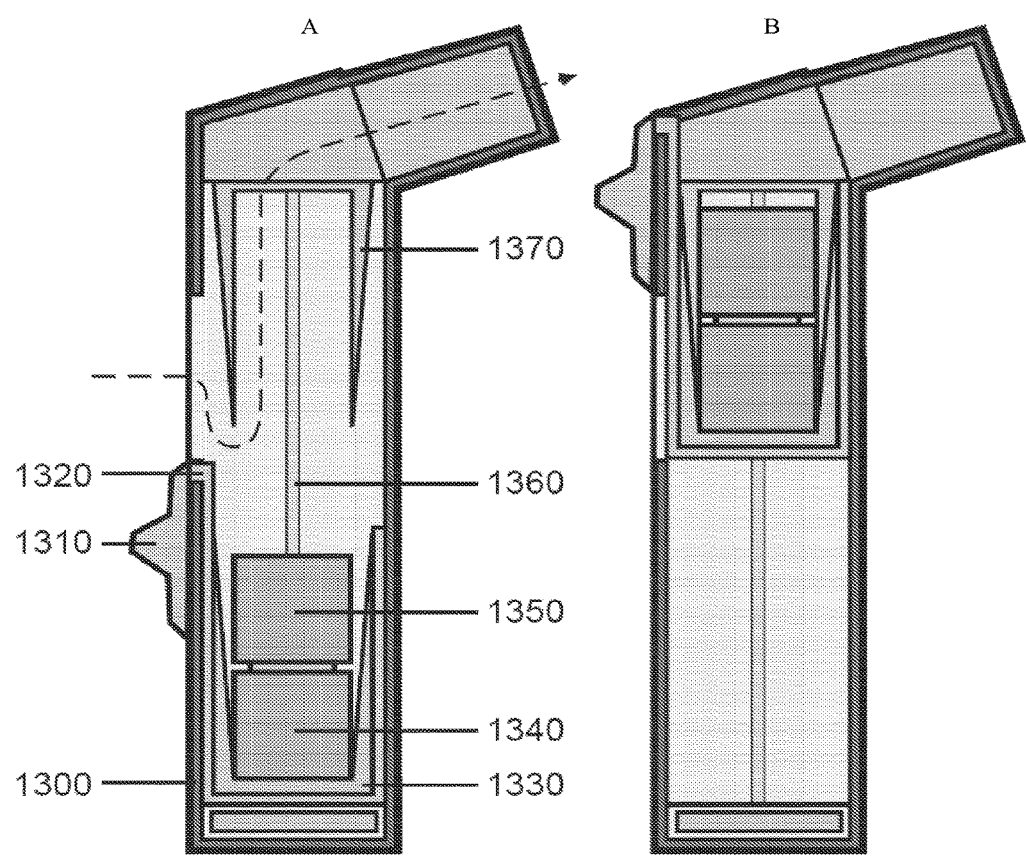
FIG. 14 a sectional view of an exemplary device simulates a metered dose inhaler commonly used for pharmaceutical delivery of inhaled medicaments.

FIG. 14 shows another variant of the device of FIG. 12. In this version, outer housing 1300 is contiguous with the moving components being switch 1310 and the various internal elements shown. Switch 1310 is connected to source seating element 1330 by a connecting bar 1320. As switch 1310 is moved up, rigid seating element 1330 moves along pole 1360. At the charging position, reservoir elements 1340 and 1350 are brought into contact with deformable element 1370 which are in also brought in contact with rigid seating element 1330. Rigid seating element 1330 is dimensioned to squeeze deformable elements 1370 into contact with reservoir elements 1340 and 1350 in the final portion of the sliding motion (FIG. 14 B). This action coats the upper portion of deformable element 1370 with, e.g., nicotine base solution from reservoir 1350 and the lower portion of deformable element 1370 with pyruvic acid from 1340 to create a nicotine source and a delivery enhancing compound source, respectively. The top surface of reservoir 1350 may be covered by an impermeable material to limit the amount of volatilization of medicament and delivery enhancing compound from the reservoirs when in the operational position (FIG. 14 A). A circular flap of flexible, impermeable material may extend from elements 1320 or 1330 to close off the volume below reservoir 1350 and further limit volatilization. In charging position (FIG. 14B) the flap would be forced down and away from the reservoirs by deformable element 1370.

Exemplary Device 10

Figure 15:
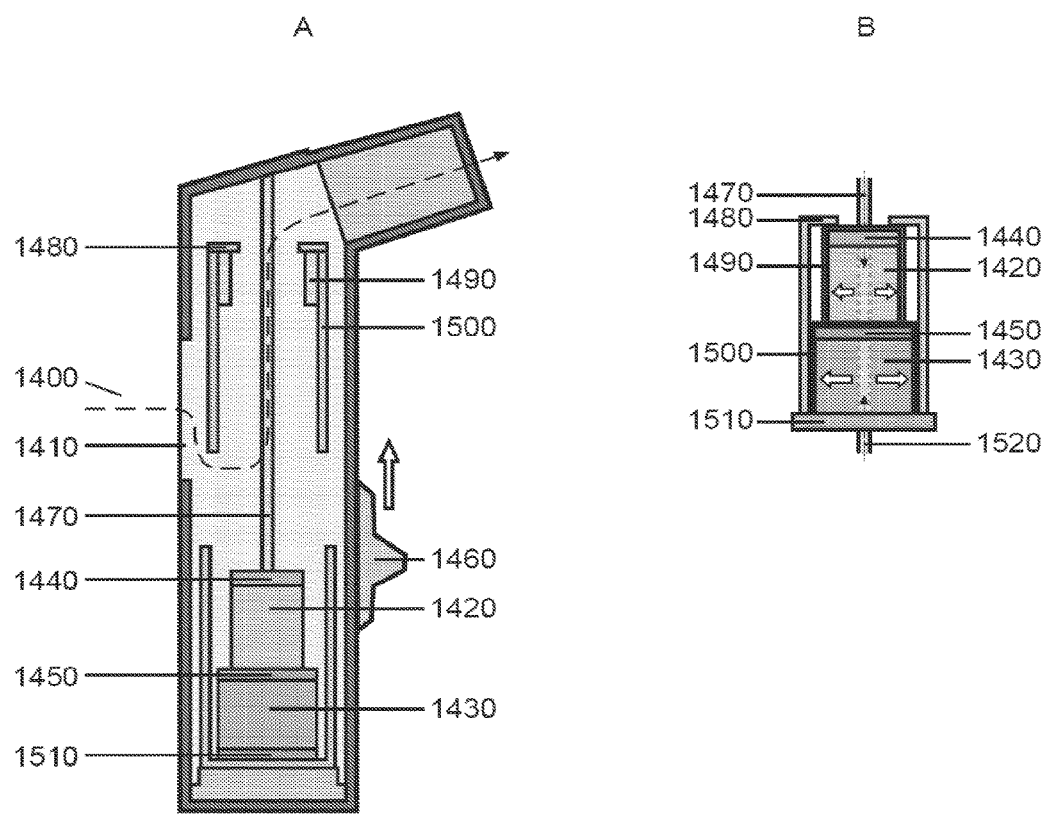
FIG. 15 a sectional view of an exemplary device simulates a metered dose inhaler commonly used for pharmaceutical delivery of inhaled medicaments.

FIG. 15 shows another delivery device configuration. FIG. 15A shows the device 1400 in use mode. Air moves from intake 1410 past delivery enhancing compound source 1500, nicotine source 1490 and through outlet 1415. The nicotine and delivery enhancing compound are coated onto the side walls of their respective sources. To recharge the sources, delivery enhancing compound reservoir 1430 and nicotine reservoir 1420 are provided. Switch 1460 may be actuated by a users thumb to recharge the sources. Upon activation by switch 1460, base 1510 is motivated along guide rod 1470 toward delivery enhancing compound source 1500 and nicotine source 1490. Shown in FIG. 15B, upon contact with the delivery enhancing compound source 1500, the nicotine source 1490 and the upper stop element 1480, impermeable caps 1440 and 1450 compress reservoirs to force delivery enhancing compound and nicotine out onto the surfaces of the sources 1490 and 1500. The reservoirs in this device may be made of any deformable adsorbing or absorbing material capable of holding the nicotine or delivery enhancing solutions. The reservoirs will generally be motivated back down guide pole 1470 automatically after recharging the sources, thus making the device a conveniently operated "one click" device. The movement of the reservoirs may be achieved by any convenient means. For example, a motive wire 1520 may be provided within a groove on guide pole 1470. The motive wire 1520 may be attached to base 1510 and motivated up and down the guide pole 1470 by a motor rotated element (not shown). In some versions of this device configuration, the top outer portion of device 1400 may be rotated to define the size of inlet 1410 analogous to element 140 shown in FIG. 4.

INDUSTRIAL APPLICABILITY

The methods and devices herein are useful for the therapeutic delivery of nicotine for smoking cessation, harm reduction and/or substitution. In addition, the devices and methods herein are useful as an alternative, general nicotine delivery system in place of tobacco based products. The methods and devices herein are further useful for the delivery of other medicaments as described herein.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

All references and other information cited to, or otherwise identified herein, are hereby incorporated by reference in their entireties as if each had been separately so incorporated. U.S. provisional patent application Ser. No. 60/909,302 filed 30 Mar. 2007; U.S. provisional patent application Ser. No. 61/160,904, filed 17 Mar. 2009; and PCT/US08/58122 filed 25 Mar. 2008 are also hereby incorporated by reference in their entireties.

The invention claimed is:

1. A device for delivering nicotine to a subject, the device comprising a housing, the housing comprising:
    a) an inlet and an outlet in communication with each other and adapted so that a gaseous carrier may pass into the housing through the inlet, through the housing and out of the housing through the outlet, the device comprising in series from inlet to outlet:
    b) a first internal area in communication with the inlet, the first internal area comprising a delivery enhancing compound source,
    c) a second internal area in communication with the first internal area, the second internal area comprising a nicotine source,
        i) the nicotine source comprising the nicotine and an electrolyte forming compound, both in an aqueous solution, wherein the nicotine comprises nicotine base, and the electrolyte forming compound comprises an alkali metal hydroxide, and
    d) optionally, a third internal area in communication with the second internal area and the outlet.

2. The device of claim 1, wherein the electrolyte forming compound is selected from the group consisting of sodium hydroxide (NaOH), potassium hydroxide (KOH), lithium hydroxide (LiOH), and combinations thereof.

3. The device of claim 1, wherein the electrolyte forming compound comprises KOH.

4. The device of claim 1, wherein the pH of the aqueous solution is equal to or greater than 9.0.

5. The device of claim 3, wherein the ratio of KOH to nicotine base (or base equivalents) is from 10:40 to 10:100.

6. The device according to claim 1, wherein the delivery enhancing compound source comprises an acid.

7. The device according to claim 6, wherein the acid is an inorganic acid or a carboxylic acid.

8. The device according to claim 7, wherein the acid is a 2-Keto acid.

9. The device according to claim 8, wherein the acid is selected from the group consisting of 3-Methyl-2-oxovaleric acid, Pyruvic acid, 2-Oxovaleric acid, 4-Methyl-2-oxo valeric acid, 3-Methyl-2-oxobutanoic acid, 2-Oxooctanoic acid and combinations thereof.

10. A device for delivering nicotine to a subject, the device comprising a housing, the housing comprising:
    a) an inlet and an outlet in communication with each other and adapted so that a gaseous carrier may pass into the housing through the inlet, through the housing and out of the housing through the outlet, the device comprising in series from inlet to outlet:
    b) a first internal area in communication with the inlet, the first internal area comprising a delivery enhancing compound source, the delivery enhancing compound comprising a carboxylic acid,
    c) a second internal area in communication with the first internal area, the second internal area comprising a nicotine source,
        i) the nicotine source comprising nicotine base and an electrolyte forming compound, both in an aqueous solution, wherein the electrolyte forming compound comprises an alkali metal hydroxide, and
    d) optionally, a third internal area in communication with the second internal area and the outlet.

11. The device of claim 10, wherein the electrolyte forming compound is selected from the group consisting of sodium hydroxide (NaOH), potassium hydroxide (KOH), lithium hydroxide (LiOH), and combinations thereof.

12. The device of claim 10, wherein the electrolyte forming compound comprises KOH.

13. The device of claim 10, wherein the pH of the aqueous solution is equal to or greater than 9.0.

14. The device of claim 12, wherein the ratio of KOH to nicotine base (or base equivalents) is from 10:40 to 10:100.

15. The device according to claim 10, wherein the acid is a 2-Keto acid.

16. The device according to claim 15, wherein the acid is selected from the group consisting of 3-Methyl-2-oxovaleric acid, Pyruvic acid, 2-Oxovaleric acid, 4-Methyl-2-oxo valeric acid, 3-Methyl-2-oxobutanoic acid, 2-Oxooctanoic acid and combinations thereof.

17. A device for delivering nicotine to a subject, the device comprising a housing, the housing comprising:
    a) an inlet and an outlet in communication with each other and adapted so that a gaseous carrier may pass into the housing through the inlet, through the housing and out of the housing through the outlet, the device comprising in series from inlet to outlet:
    b) a first internal area in communication with the inlet, the first internal area comprising a delivery enhancing compound source, the delivery enhancing compound source comprising a 2-keto carboxylic acid;
    c) a second internal area in communication with the first internal area, the second internal area comprising a nicotine source,
        i) the nicotine source comprising nicotine base and an electrolyte forming compound, both in an aqueous solution, wherein the electrolyte forming compound comprises an alkali metal hydroxide, and the nicotine base and the electrolyte forming compound are present at a weight ratio of 10:20 to 10:125; and
    d) optionally, a third internal area in communication with the second internal area and the outlet.

18. The device of claim 17, and wherein the electrolyte forming compound is selected from the group consisting of sodium hydroxide (NaOH), potassium hydroxide (KOH), lithium hydroxide (LiOH), and combinations thereof.

19. The device of claim 17, wherein nicotine is selected from nicotine base, nicotine bitartrate and combinations thereof and the electrolyte forming compound comprises KOH.

20. The device of claim 17, wherein the pH of the aqueous solution is equal to or greater than 9.0.

21. The device of claim 19, wherein the ratio of KOH to nicotine base (or base equivalents) is from 10:40 to 10:100.

22. The device according to claim 17, wherein the acid is selected from the group consisting of 3-Methyl-2-oxovaleric acid, Pyruvic acid, 2-Oxovaleric acid, 4-Methyl-2-oxo valeric acid, 3-Methyl-2-oxobutanoic acid, 2-Oxooctanoic acid and combinations thereof.

* * * * *